United States Patent
Chen et al.

(10) Patent No.: US 8,663,236 B2
(45) Date of Patent: Mar. 4, 2014

(54) TRANSGASTRIC ABDOMINAL ACCESS

(75) Inventors: Eugene G. Chen, Carlsbad, CA (US); Vahid C. Saadat, Saratoga, CA (US); Rebecca S. Inderbitzen, San Diego, CA (US); Lee L. Swanstrom, Portland, OR (US)

(73) Assignee: USGI Medical Inc., San Clemente, CA (US)

( * ) Notice: Subject to any disclaimer, the term of this patent is extended or adjusted under 35 U.S.C. 154(b) by 1620 days.

(21) Appl. No.: 11/238,279

(22) Filed: Sep. 28, 2005

(65) Prior Publication Data

US 2006/0237022 A1    Oct. 26, 2006

Related U.S. Application Data

(60) Provisional application No. 60/675,061, filed on Apr. 26, 2005, provisional application No. 60/699,414, filed on Jul. 13, 2005.

(51) Int. Cl.
*A61F 11/00* (2006.01)

(52) U.S. Cl.
USPC .......................................... 606/108; 128/898

(58) Field of Classification Search
USPC ............. 604/164, 164.01; 606/144, 145, 106, 606/108, 158, 24; 623/23.65; 128/898
See application file for complete search history.

(56) References Cited

U.S. PATENT DOCUMENTS

| | | | |
|---|---|---|---|
| 4,235,238 A | 11/1980 | Ogiu et al. | |
| 5,167,627 A * | 12/1992 | Clegg et al. | 604/103.03 |
| 5,174,276 A * | 12/1992 | Crockard | 600/104 |
| 5,297,536 A | 3/1994 | Wilk | |
| 5,458,131 A | 10/1995 | Wilk | |
| 5,507,754 A * | 4/1996 | Green et al. | 606/139 |
| 6,071,292 A * | 6/2000 | Makower et al. | 606/158 |
| 6,572,629 B2 | 6/2003 | Kalloo et al. | |
| 6,599,303 B1 * | 7/2003 | Peterson et al. | 606/153 |
| 6,991,602 B2 | 1/2006 | Nakazawa et al. | |
| 7,931,661 B2 | 4/2011 | Saadat et al. | |
| 2001/0049497 A1 * | 12/2001 | Kalloo et al. | 604/164.01 |
| 2003/0216613 A1 | 11/2003 | Suzuki et al. | |
| 2005/0216041 A1 | 9/2005 | Okada et al. | |
| 2005/0222492 A1 | 10/2005 | Adams | |
| 2006/0036267 A1 | 2/2006 | Saadat et al. | |
| 2006/0237022 A1 | 10/2006 | Chen et al. | |

* cited by examiner

*Primary Examiner* — Thomas J Sweet
*Assistant Examiner* — Christopher D Prone
(74) *Attorney, Agent, or Firm* — Kenneth H. Ohriner; Perkins Coie LLP

(57) ABSTRACT

Transgastric abdominal access methods and apparatus are described herein. A shape-lockable elongate body can be advanced endoluminally in a flexible state into the stomach, where an opening is created through the stomach wall. The opening can be created endoluminally or by incising instruments placed through the abdominal wall. The elongate body can be transitioned to a rigid state prior to, during, or after advancement into the patient and is passed through the opening into the peritoneal cavity. A dilation balloon can be positioned simultaneously within the elongate body and within the tissue opening such that the elongate body can be advanced through the tissue opening. A flexible needle catheter can also be delivered through the elongate body or an endoscope to provide for insufflation prior to cutting or piercing through the stomach wall. Also, tissue closure devices and methods to close the opening created through the stomach wall.

12 Claims, 42 Drawing Sheets

TRANSGASTRIC ABDOMINAL ACCESS

CROSS-REFERENCES TO RELATED APPLICATIONS

This application claims the benefit of priority to U.S. Prov. Pat. App. Ser. Nos. 60/675,061 (USGI 3000US), filed Apr. 26, 2005 and 60/699,414, filed Jul. 13, 2005, each of which is incorporated herein by reference in its entirety.

BACKGROUND OF THE INVENTION

1. Field of the Invention

The present invention relates to apparatus and methods for transluminal access into a patient body. More particularly, the present invention relates to apparatus and methods for endoluminal transgastric access into regions within the peritoneal space utilizing endoluminal and trans-abdominal access for performing therapeutic and/or diagnostic procedures; also related are methods and apparatus for closing or approximating tissue openings created for the therapeutic and/or diagnostic procedures.

In an effort to reduce the invasiveness of treatments for gastrointestinal ("GI") disorders, gastroenterologists, GI surgeons and others are pursuing minimally invasive endoluminal treatments for such disorders. Treatments through natural GI passageways are being pursued utilizing instruments advanced per-orally and/or per-anally. For example, U.S. Pat. No. 6,572,629 (Kallo et al.); U.S. Pat. No. 5,297,536 (Wilk); and U.S. Pat. No. 5,458,131 (Wilk), which are incorporated herein by reference in their entirety, show tools and methods for entry into the peritoneal space through the stomach wall.

In view of advances in methods and apparatus for minimally invasive endoluminal GI treatment, it would be desirable to provide methods and apparatus for diagnostic or therapeutic treatment of organs of the digestive system or other parts of the body via instruments advanced per-orally and transgastrically and/or per-anally, or a combination thereof.

Transgastric procedures from the interior of the stomach to the exterior have also been described previously in U.S. Pat. Pub. No. 2003/0216613 A1 (Suzuki et al.) However, while that reference discusses curvable overtubes that may be maintained in a curve, it does not describe an overtube or guide that may be shape-locked or rigidized along its length.

During endoluminal access into the peritoneal cavity of a patient, once the stomach tissue has been pierced and dilated, insufflation of the stomach is no longer possible. Thus, once the endoscope or instruments are removed from the peritoneal space and withdrawn proximally from the opening within the stomach wall, relocating this opening for closure becomes very difficult for the physician. This problem is compounded by the inability to insufflate the stomach to gain a clear view of the surrounding stomach tissue as well as by the limitations of endoluminal visualization within the stomach.

Accordingly, there is also a need for marking or otherwise indicating the location of an opening made within a stomach wall for closing the opening upon the end of a procedure.

BRIEF SUMMARY OF THE INVENTION

Methods and apparatus are provided for accessing digestive or other organs (as well as other parts of the body) within the gastrointestinal tract and within the peritoneal cavity. Such regions may be accessed endoluminally and transluminally via instruments passed into the gastrointestinal tract per-orally and/or per-anally and, e.g., transluminally, out of the stomach for performing diagnostic or therapeutic surgical procedures.

In one aspect for endoluminally accessing the peritoneal cavity within the patient body, a shape-lockable elongate body may be advanced in a flexible state through a natural orifice, e.g., the patient's mouth, into the patient body, e.g., stomach. An opening may be created through the tissue wall, e.g., the stomach wall, for accessing the space external to the stomach. The opening through the tissue wall may be created by advancing an incising instrument endoluminally through the patient body. Alternatively, instruments may be passed through the abdominal wall of the patient and into the peritoneal cavity to incise a region of the tissue wall from its exterior surface to create an access opening for the endoluminally delivered instruments into the peritoneal cavity. Moreover, visualization may be facilitated during procedures by additional imaging tools positioned through the abdominal wall. Once the opening has been made, either endoluminally or trans-abdominally, any incisions in the abdominal wall may be closed prior to, during, or after completion of a procedure within the peritoneal cavity of the patient. At least the distal portion of the elongate body may be passed through the opening for providing access to the peritoneal cavity. The elongate body may be transitioned from its flexible state to a rigid state prior to, during, or after advancing the elongate body into the patient.

In another aspect, the shape-lockable elongate body may be advanced in its flexible state and the opening may be created through the tissue wall, as above. But a dilation balloon may be advanced through the elongate body and positioned at least partially within the opening within the tissue and within a distal opening of the elongate body. The dilation balloon may then be expanded such that the distal opening of the elongate body is obstructed by the dilation balloon and the opening through the tissue wall is dilated. With the dilation balloon maintained in its position within the distal opening of the elongate body, the elongate body may be advanced through the dilated opening of the tissue wall.

In passing an endoscope through the stomach wall, a number of different methods and tools may be employed. For instance, an ablation probe or needle knife may be advanced through the endoscope lumen into proximity with the stomach wall. The probe or needle knife may be actuated to pierce or cut through the stomach wall to create a gastric opening into the peritoneal cavity. Once a gastric opening of sufficient size, i.e., at least sufficiently large enough to pass a guidewire or probe therethrough, has been created, the needle knife may be removed and a conventional guidewire may be advanced therethrough until the guidewire is passed at least partially within peritoneal cavity.

With the guidewire in place, a dilation balloon having an expanded diameter of, e.g., 18 or 20 mm (or greater), may be passed in its unexpanded profile over the guidewire until the dilation balloon is positioned within the gastric opening, where it may then be expanded to thereby dilate the gastric opening. Once the gastric opening has been desirably dilated, the balloon may be deflated and withdrawn. The guidewire may also be withdrawn proximally, if so desired. The endoscope may then be advanced distally through the dilated gastric opening for entry into the peritoneal cavity where any number of diagnostic or therapeutic procedures may be undertaken. While the endoscope body is advanced, the shapelock elongate body may be maintained in its rigidized state while held static relative to the stomach wall to provide a stable platform for endoscope advancement. Alternatively, the elongate body may be advanced distally in its rigidized or flexible state through the dilated gastric opening along with the endoscope body.

In another example for transgastrically accessing the peritoneal cavity, the shapelock elongate body may be placed directly against the stomach wall at a tissue contact region such that the elongate body provides some stability against the tissue surface during the procedure. The elongate body may be rigidized any time during the procedure relative to the stomach wall. If the elongate body is placed directly against a tissue contact region on the stomach wall over the gastric opening, the elongate body may be rigidized, as mentioned above, to provide for stability during the procedure.

Additionally and/or optionally, one or more retractable tissue anchors may be projected distally from within the end of elongate body and extended into and/or through tissue contact region to temporarily anchor the distal end of the elongate body to the region of stomach wall. The retractable tissue anchors may be configured as wires, hooks, barbs, corkscrews, etc., which are positioned within the walls of the elongate body for delivery through the patient and which may be urged distally to extend from the elongate body for engagement against or to the stomach wall. If the retractable tissue anchors are configured as wires, they may be comprised of a shape memory alloy such as Nitinol which remain in a straightened configuration but conform into a hooked configuration once free of any constraints.

The elongate body, either in its rigidized or flexible state, may then be advanced distally through the dilated gastric opening and further advanced into the peritoneal cavity, if so desired. Having an inflated dilation balloon retained within the shapelock lumen may minimize any transition step or region between the balloon and the elongate body to facilitate the passage of the elongate body through the dilated opening.

In yet another variation, the elongate body may be advanced into and through the gastric opening utilizing the endoscope, which may already be advanced through the gastric opening. With the elongate body positioned within the stomach and the steerable distal portion of the endoscope positioned externally of the stomach within the peritoneal cavity, the steerable distal portion may be retroflexed such that its distal end faces the exterior of the stomach wall. While maintaining the retroflexed configuration of the steerable distal portion, the body of the endoscope may be withdrawn proximally through the elongate body (or the elongate body may be pushed distally over the endoscope) until the stomach tissue surrounding the gastric opening is pushed over or onto a portion of the elongate body by the retroflexed steerable portion. Once a portion of the elongate body has been urged through the gastric opening, the surrounding tissue may optionally be anchored or otherwise adhered temporarily to the exterior of the elongate body through a variety of mechanisms, e.g., balloons, expandable mesh, retractable wires or barbs, etc., and the steerable distal portion may be straightened and further advanced into the peritoneal cavity to effect any number of diagnostic or therapeutic procedures. Alternatively, rather than using an endoscope, a specially adapted tissue retraction instrument may be utilized instead.

In yet another variation, the elongate body may be positioned adjacent to or against the gastric opening in a rigidized or flexible state. Once the elongate body has been desirably positioned, one or more deployable retraction members may be projected from the distal end of the elongate body. Such retraction members may be fabricated from a shape memory alloy, e.g., Nitinol, such that when positioned within its respective retraction member lumens, the retraction members are configured in a straightened shape for delivery. However, when first urged distally from the elongate body, the retraction members may be biased to initially converge towards a longitudinal axis of the elongate body to facilitate the initial insertion of the retraction members into and through the gastric opening.

The retraction members may be urged until the retained surrounding tissue is pushed over or upon the outer surface of the elongate body. Once the tissue around the gastric opening has been desirably pushed over the elongate body, the retraction members may be withdrawn back into the elongate body. Alternatively, the position of the elongate body and the retraction members may be maintained through the gastric opening and the endoscope may be advanced through the shapelock lumen and into the peritoneal cavity.

Another aspect of transgastric access may include adequate insufflation of the peritoneal cavity and/or stomach during advancement of an instrument through the stomach wall. When advancing a needle knife or ablation tool through the stomach wall, the physician may risk inadvertently cutting or piercing into any number of body structures, e.g., the peritoneal and/or abdominal wall, liver, aortic artery, etc., adjacent to the stomach through which a gastric opening is to be formed. Thus, one method for facilitating the safe incision through a stomach wall and into the peritoneal cavity may include the use of a flexible needle catheter or guidewire which may be deliverable through the endoscopic working lumen.

Flexible needle catheter or guidewire may include a hollow catheter or hollow guidewire having a needle body with a needle lumen defined therethrough attached to the distal end of the catheter or guidewire. Alternatively, the distal end of the needle catheter may be tapered into a piercing tip. The needle body may be advanced distally out of the elongate body and/or endoscope to pierce through the portion of the stomach wall to create the gastric opening. Once the needle body has just pierced through the stomach wall, it may be advanced slowly into the peritoneal cavity and a fluid or gas, e.g., water, saline, carbon dioxide, nitrogen, air, etc., may be pumped into the peritoneal cavity to insufflate the region, e.g., ≤15 mmHg, to lift adjacent body structures away from the external surface of the stomach wall. Accordingly, a pump located external to the patient body may be fluidly connected via a fluid line through the elongate body to the needle catheter or guidewire. Once the region surrounding the gastric opening has been sufficiently insufflated, a needle knife, ablation probe, or other instrument may be passed through the gastric opening or stomach wall without hitting any adjacent body structures.

Once a procedure has been completed within the peritoneal cavity, maintaining the location of the opening along the stomach wall may be desirable once the elongate body has been removed from the opening to facilitate the closure of the opening after the procedure has been completed within the peritoneal space.

One example is a marker assembly having an elongate flexible body with an inflatable balloon member reconfigurable between a low-profile advancement configuration and an expanded marking configuration. The inflatable member may have an expanded diameter which is larger than that of the elongate body and which is also larger than the opening. In use, prior to withdrawing the elongate body from the opening along the stomach wall, the elongate flexible body and expandable member may be advanced through a working lumen into the peritoneal space. Once the expandable member has been sufficiently advanced past the lumen opening, the expandable member may be expanded. With the mesh member in its expanded shape, the flexible member may optionally be withdrawn proximally until the mesh member is resting against the outer serosal tissue layer of stomach. The expanded profile prevents the pulling of the expandable member proximally back through the opening and may now serve as a marker for easily locating the position of opening.

With the marker in place distally of the opening, the expandable member may be used as a platform for facilitating the grasping and manipulating of the overlying tissue against the expandable member by the assembly. Once the tissue anchors have been deployed adjacent to the opening, the mesh member may be reconfigured into its low-profile configuration and withdrawn proximally back into the stomach through the opening via the flexible body. The tissue anchors may then be cinched or approximated towards one another to thereby close the opening.

Alternatively, the elongate body may be advanced into the stomach and positioned adjacent to a tissue region of interest through which the elongate body and/or tools are to be advanced through and into the peritoneal space. Prior to piercing and/or dilating an opening along the stomach wall, the tissue anchors may be deployed along the tissue region of interest. With the tissue area marked by the deployed tissue anchors, the lumen opening of the elongate body may be repositioned or advanced against and/or through the tissue region and an opening may be formed or dilated in the tissue adjacent or proximate to the anchors.

BRIEF DESCRIPTION OF THE DRAWINGS

FIGS. 7A to 7C show a flexible catheter or guidewire device having a tissue piercing tip adapted to be advanced through the tissue wall and into the peritoneal space for insufflating the space prior to or during endoscope advancement through the tissue wall.

DETAILED DESCRIPTION OF THE INVENTION

The present invention relates to apparatus and methods for endoluminal, transluminal procedures, including per-oral, transgastric and/or per-anal, transcolonic procedures. Access to regions within the body may be effected through a per-oral and transgastric approach where access to regions within a patient body, i.e., regions which are normally accessible through open or laparoscopic surgical procedures, may be accomplished through endoluminal methods and devices delivered endoluminally. For instance, access to a patient's peritoneal cavity may be accomplished entirely through endoluminal methods and devices via passage through an opening made in the stomach wall. Alternatively, endoluminal access may also be facilitated through a number of combined endoluminal and laparoscopic procedures.

Figure 1A:
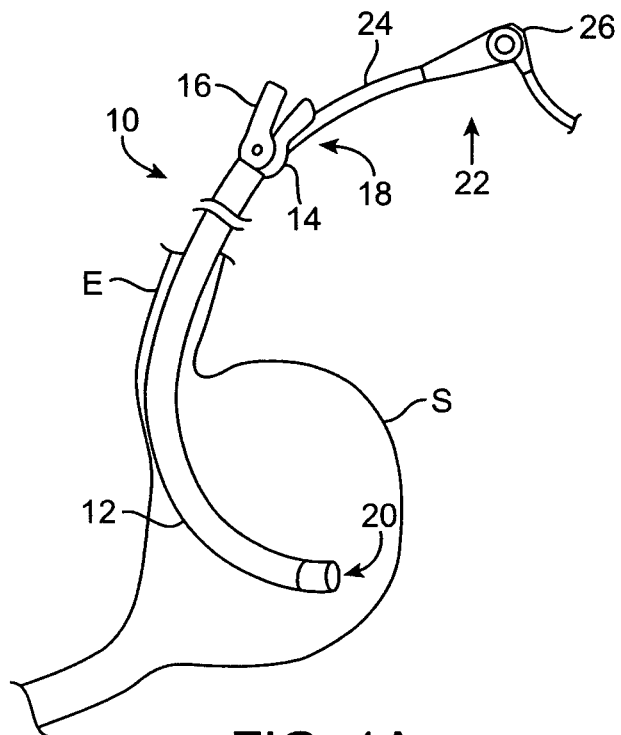
FIGS. 1A and 1B show a shape-lockable apparatus advanced endoluminally into a stomach with an endoscope placed therethrough and positioned for transgastric advancement into a peritoneal space of a patient.
Figure 1B:
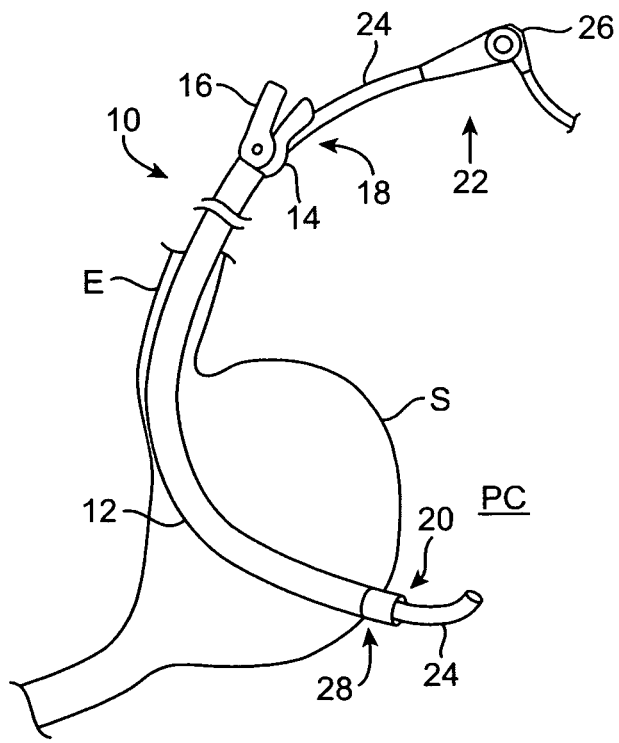

Examples of endoluminal methods and instruments are first described below. With reference to FIGS. 1A and 1B, a shape-lockable assembly 10 is shown having been advanced per-orally, through the esophagus E, and into the stomach S of a patient. Shape-lockable assembly 10 may comprise, in part, a flexible and elongate shape-locking body 12 which may utilize a plurality of locking links which enable the elongate body 12 to transition between a flexible state and a rigidized or shape-locked configuration. Details of such a shape-lockable body may be seen in further detail in U.S. Pat. Nos. 6,783,491; 6,790,173; and 6,837,847, each of which is incorporated herein by reference in its entirety.

Additionally, the elongate body 12 may also incorporate additional features that may enable any number of therapeutic procedures to be performed endoluminally. An elongate body 12 may be accordingly sized to be introduced per-orally. However, the elongate body may also be configured in any number of sizes, for instance, for advancement within and for procedures in the lower gastrointestinal tract, such as the colon.

The assembly, in one variation, may have several separate controllable bending sections along its length to enable any number of configurations for the elongate body 12. For instance, in one variation, elongate body 12 may further comprise a bending section located distal of the elongate body 12; the bending section may be configured to bend in a controlled manner within a first and/or second plane relative to the elongate body 12. In yet another variation, the elongate body 12 may further comprise another bending section located distal of the first bending section. In this variation, the bending section may be configured to articulate in multiple planes, e.g., 4-way articulation, relative to the first bending section and elongate body 12. In a further variation, a third bending section may also be utilized along the length of the device.

In yet another variation, each of the bending sections and the elongate body may be configured to lock or shape-lock its configuration into a rigid set shape once the articulation has been desirably configured. An example of such an apparatus having multiple bending sections which may be selectively rigidized between a flexible configuration and a shape-locked configuration may be seen in further detail in U.S. Pat. Pubs. 2004/0138525 A1; 2004/0138529 A1; 2004/0249367 A1; and 2005/0065397 A1, each of which is incorporated herein by reference in its entirety.

As the bending sections may be articulated in any number of configurations via control wires routed through the elongate body, the assembly 10 may be actively steered to reach all areas of the stomach. The bending features may be controlled via a handle 14 attached to a proximal end of elongate body 12 and a rigidization actuation lever 16 may be manipulated to actuate the transition between rigid and flexible states of elongate body 12. Handle 14 may also define an entry port 18 therethrough which allows for passage of any number of endoluminal instruments through handle 14 from outside the patient body and into at least one working lumen 20 defined through the length of elongate body 12 for passage into the patient body.

Once a desired position is achieved within a patient body, e.g., within stomach S, the elongate body 12 may be locked or rigidized in place, as shown in FIG. 1A. An endoscope 22, controllable via endoscope handle 26 attached thereto, may be passed through shapelock assembly handle 14 for insertion into the patient body through lumen 20. Alternatively, endoscope 22 may be advanced endoluminally through the patient simultaneously along with elongate body 12. In either case, once elongate body 12 has been desirably positioned and rigidized near or against an interior region of the stomach S, the endoscope body 24 and/or the shapelock elongate body 12 may be pierced through or otherwise passed through gastric opening 28 formed through the stomach wall and advanced through or into the peritoneal cavity PC of the patient, as shown in FIG. 1B. Once endoscope 24 and/or elongate body 12 are positioned within the peritoneal cavity PC, any number of diagnostic or therapeutic procedures may be performed.

Various other apparatus and methods for transgastric advancement through a gastric wall for access into the peritoneal space are disclosed in greater detail in U.S. patent application Ser. No. 10/918,217 filed Aug. 11, 2004, which is incorporated herein by reference in its entirety.

Figure 2A:
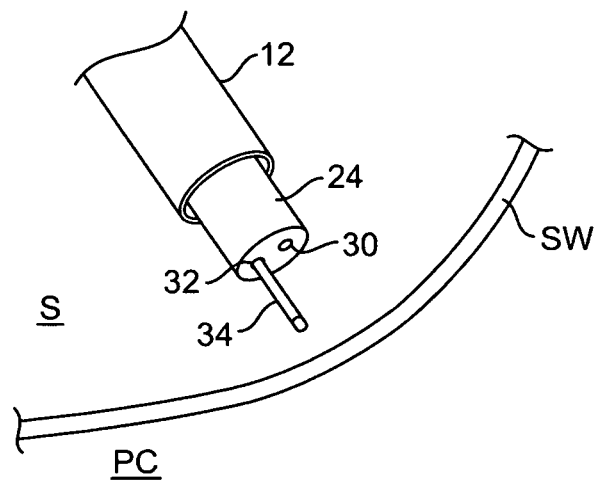
FIGS. 2A to 2E show one example for passing an endoscope through an elongate shape-locking instrument transgastrically into the peritoneal space through a dilated gastric opening.

In passing endoscope 24 through the stomach wall SW, a number of different methods and tools may be employed. For instance, FIGS. 2A to 2E show one example for passing endoscope 24 through the elongate shape-locking body 12 transgastrically into the peritoneal cavity PC through dilated gastric opening 28. Once elongate body 12 has been desirably positioned adjacent to or near a region of stomach wall SW, an ablation probe or needle knife 34 may be advanced through endoscope lumen 32 into proximity with stomach wall SW, as shown in FIG. 2A. Visualization may be provided by imaging lumen 30 of endoscope 24.

Figure 2B:
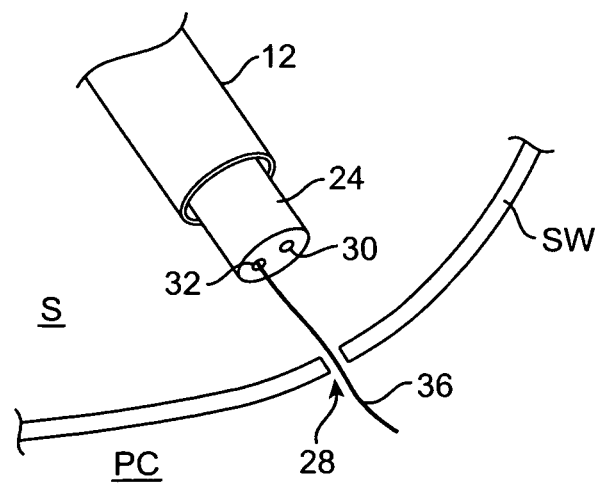

The probe or needle knife 34 may be actuated to pierce or cut through stomach wall SW at the tissue region of interest to create a gastric opening 28 into the peritoneal cavity PC. Once a gastric opening 28 of sufficient size, i.e., at least sufficiently large enough to pass a guidewire or probe therethrough, has been created in stomach wall SW, needle knife 34 may be removed from endoscopic lumen 32 and a conventional guidewire 36 may be advanced therethrough until guidewire 36 is passed at least partially within peritoneal cavity PC, as shown in FIG. 2B.

Figure 2C:
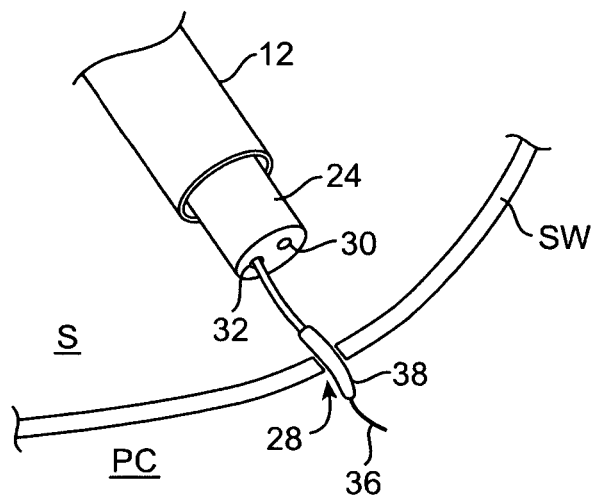
Figure 2D:
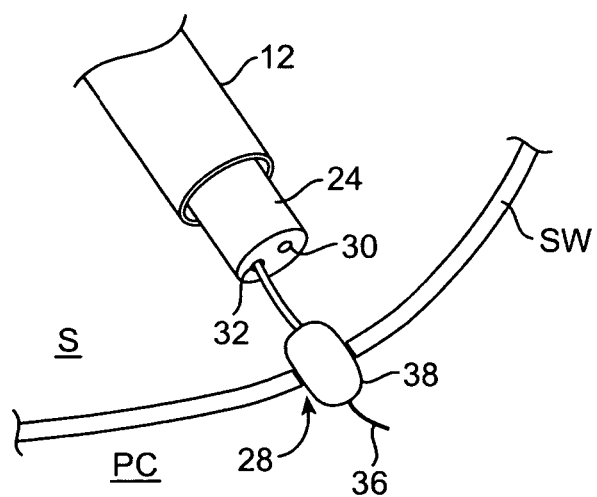
Figure 2E:
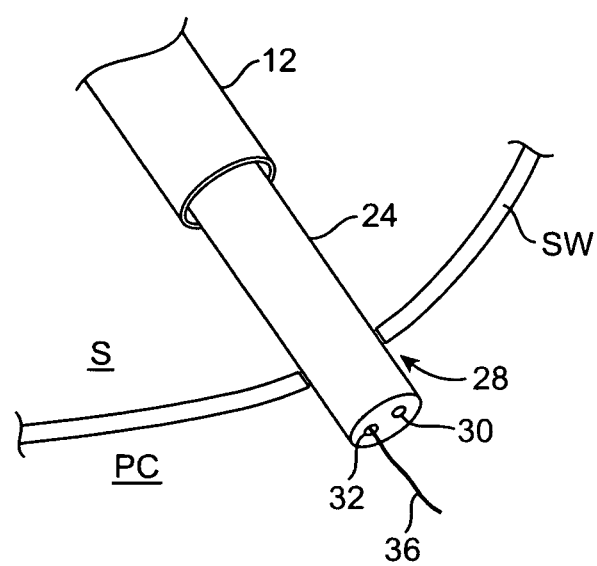

With guidewire 36 in place, a dilation balloon 38 having an expanded diameter of, e.g., 18 or 20 mm (or greater), may be passed in its unexpanded profile over guidewire 36 through endoscope lumen 32 until dilation balloon 38 is positioned within gastric opening 28, as shown in FIG. 2C. Dilation balloon 38 may then be expanded to thereby dilate gastric opening 28 to a diameter sufficient to allow for passage of at least endoscope body 24. Once gastric opening 28 has been desirably dilated, as shown in FIG. 2D, the balloon 38 may be deflated and withdrawn proximally through endoscope lumen 32. Guidewire 36 may also be withdrawn proximally, if so desired. Endoscope body 24 may then be advanced distally through the dilated gastric opening 28 for entry into the peritoneal cavity PC, as shown in FIG. 2E, where any number of diagnostic or therapeutic procedures may be undertaken. While endoscope body 24 is advanced distally through gastric opening 28, shapelock elongate body 12 may be maintained in its rigidized state while held static relative to stomach wall SW to provide a stable platform for endoscope advancement. Alternatively, elongate body 12 may be advanced distally in its rigidized or flexible state through dilated gastric opening 28 along with endoscope body 24.

Figure 3A:
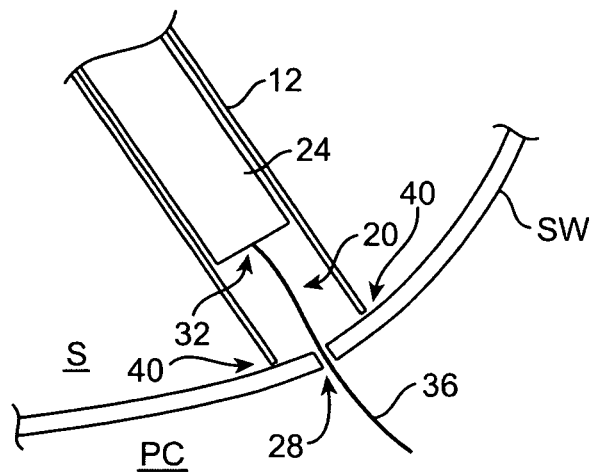
FIGS. 3A to 3E show another example for passing an endoscope and shapelock instrument into the peritoneal space by advancing both instruments through a gastric opening via a dilation balloon positioned within the shapelock instrument.

In another example for transgastrically accessing the peritoneal cavity PC, FIGS. 3A to 3E illustrate passing an endoscope and shapelock instrument into the peritoneal cavity PC by advancing both instruments through a dilated gastric opening 28 via dilation balloon 38 positioned within the shapelock lumen 20. In use, once gastric opening 28 has been formed, as described above, shapelock elongate body 12 may be advanced and positioned adjacent to or directly against stomach wall SW over gastric opening 28 and guidewire 36 may be passed through the endoscope working lumen 32, through gastric opening 28, and into peritoneal cavity PC, as shown in FIG. 3A. Elongate body 12 may be optionally locked into its rigidized state prior to, during, or after positioning elongate body 12 relative to the stomach wall. Shapelock elongate body 12 may be placed directly against the stomach wall SW, as mentioned, along a tissue contact region 40 such that elongate body 12 may provide some stability against the tissue surface during the procedure. The elongate body 12 may be rigidized any time during the procedure relative to the stomach wall SW although elongate body 12 is preferably, but not necessarily, rigidized prior to advancing the dilation balloon through gastric opening 28, as described below.

Figure 3B:
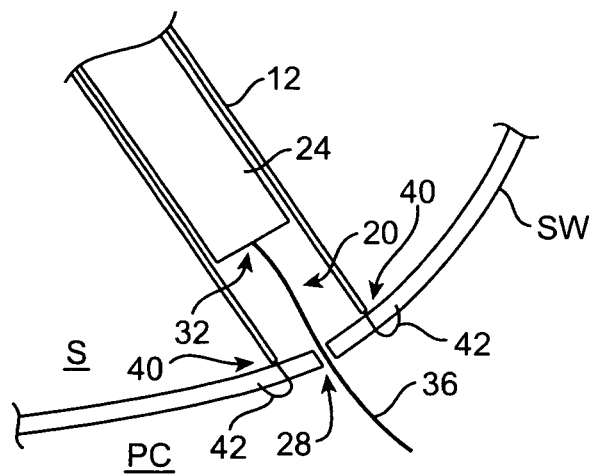

If elongate body 12 is placed directly against a tissue contact region 40 on stomach wall SW over gastric opening 28, elongate body 12 may be rigidized, as mentioned above, to provide for stability during the procedure. Additionally and/or optionally, one or more retractable tissue anchors 42 may be projected distally from within the end of elongate body 12 and extended into and/or through tissue contact region 40 to temporarily anchor the distal end of elongate body 12 to the region of stomach wall SW. Retractable tissue anchors 42 may be configured as wires, hooks, barbs, corkscrews, etc., which are positioned within the walls of elongate body 12 for delivery through the patient and which may be urged distally to extend from elongate body 12 for engagement against or to the stomach wall SW. If retractable tissue anchors 42 are configured as wires, they may be comprised of a shape memory alloy such as Nitinol which remain in a straightened configuration but conform into a hooked configuration once free of any constraints, as shown in FIG. 3B.

Figure 3C:
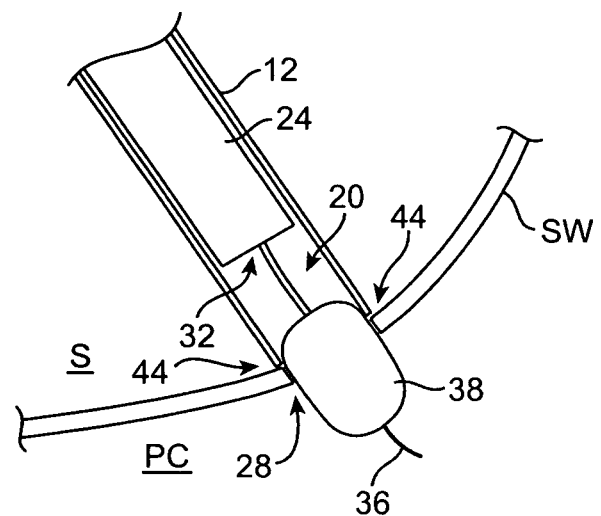

Regardless of whether retractable tissue anchors 42 are utilized, once guidewire 36 has been passed through gastric opening 28 and into peritoneal cavity PC, dilation balloon 38 may be passed through endoscope lumen 32 over guidewire 36 until balloon 38 is partially through gastric opening 28 and also partially within the shapelock lumen 20. Dilation balloon 38, while still retained at least partially within shapelock lumen 20, may then be inflated or expanded to dilate gastric opening 28, as shown in FIG. 3C.

Figure 3D:
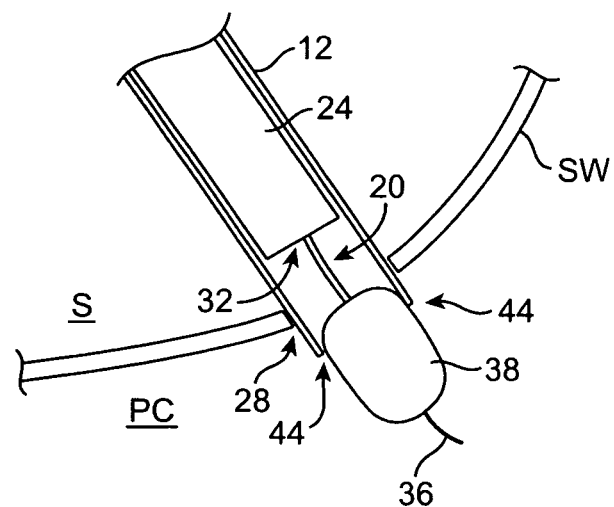
Figure 3E:
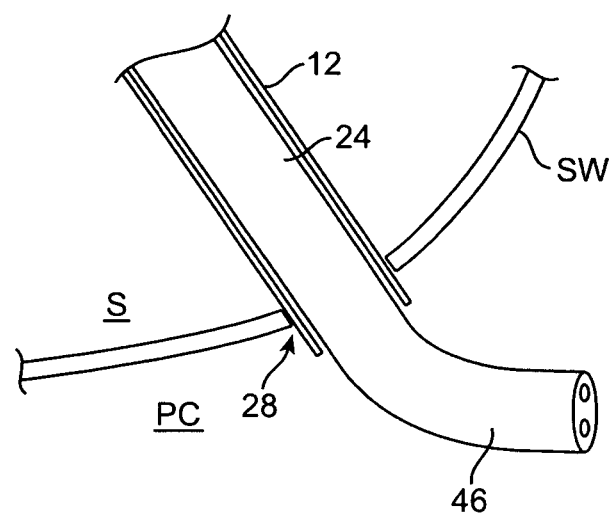

Elongate body 12, either in its rigidized or flexible state, may then be advanced distally through the dilated gastric opening 28, as shown in FIG. 3D, and further advanced into the peritoneal cavity PC, if so desired. Having an inflated dilation balloon 38 retained within shapelock lumen 20 may minimize any transition step or region 44 between balloon 38 and elongate body 12 to facilitate the passage of elongate body 12 through dilated gastric opening 28. Once elongate body 12 is passed through gastric opening 28, dilation balloon 38 may be deflated and withdrawn and endoscope 24 may be advanced into peritoneal cavity PC, as shown in FIG. 3E, where endoscope 24 may then be directed via its steerable distal portion 46 to perform any number of diagnostic or therapeutic procedures within the peritoneal cavity PC.

Figure 4A:
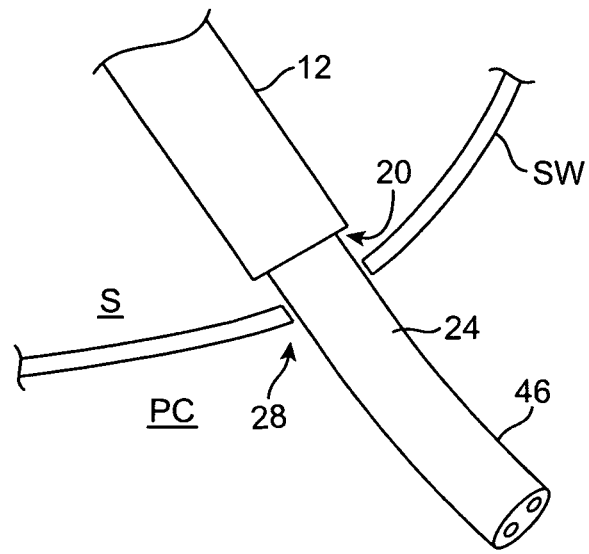
FIGS. 4A to 4D show yet another example for passing an endoscope and shapelock instrument transgastrically by urging tissue around the gastric opening over the shapelock instrument via a retroflexed endoscope.
Figure 4B:
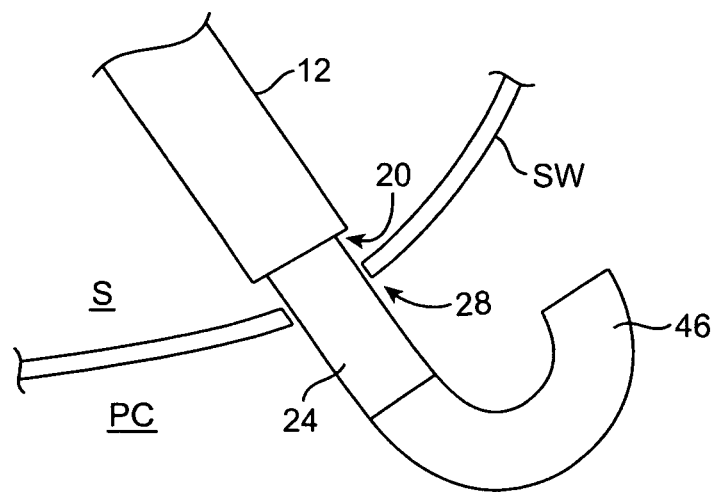

In yet another variation, elongate body 12 may be advanced into and through gastric opening 28 utilizing the endoscope 24, which may already be advanced through gastric opening 28, as described above and as shown in FIG. 4A. With elongate body 12 positioned within the stomach S and the steerable distal portion 46 of endoscope 24 positioned externally of the stomach S within the peritoneal cavity PC, steerable distal portion 46 may be retroflexed such that its distal end faces the exterior of the stomach wall SW, as shown in FIG. 4B.

Figure 4C:
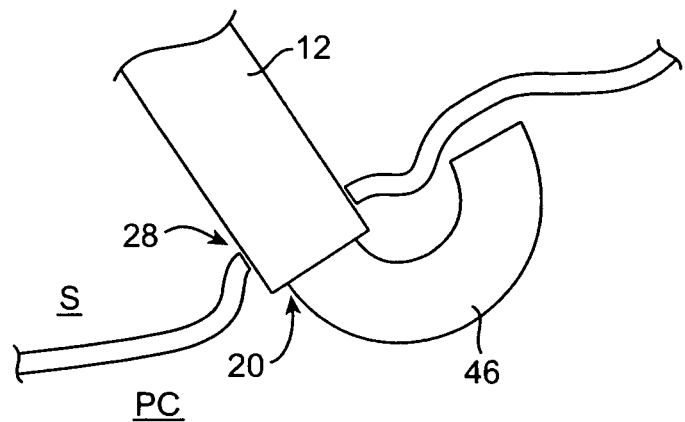
Figure 4D:
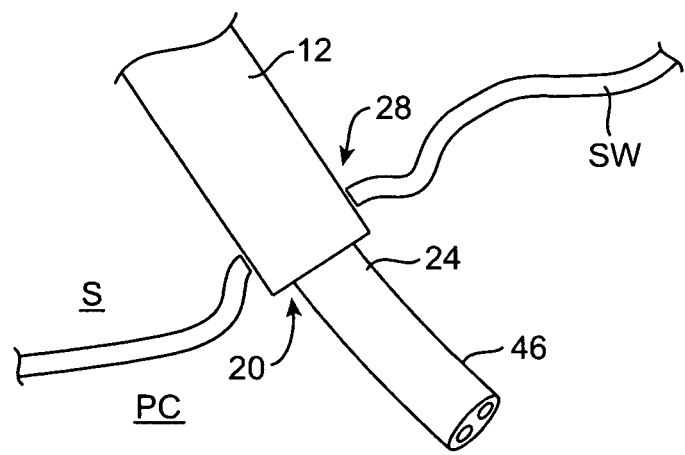

While maintaining the retroflexed configuration of steerable distal portion 46, the body of endoscope 24 may be withdrawn proximally through elongate body 12 (or elongate body 12 may be pushed distally over endoscope 24) until the stomach tissue surrounding gastric opening 28 is pushed over or onto a portion of elongate body 12 by the retroflexed steerable portion 46, as shown in FIG. 4C. Once a portion of elongate body 12 has been urged through gastric opening 28, the surrounding tissue may optionally be anchored or otherwise adhered temporarily to the exterior of elongate body 12 through a variety of mechanisms, e.g., balloons, expandable mesh, retractable wires or barbs, etc., and steerable distal portion 46 may be straightened and further advanced into the peritoneal cavity PC to effect any number of diagnostic or therapeutic procedures.

Figure 5A:
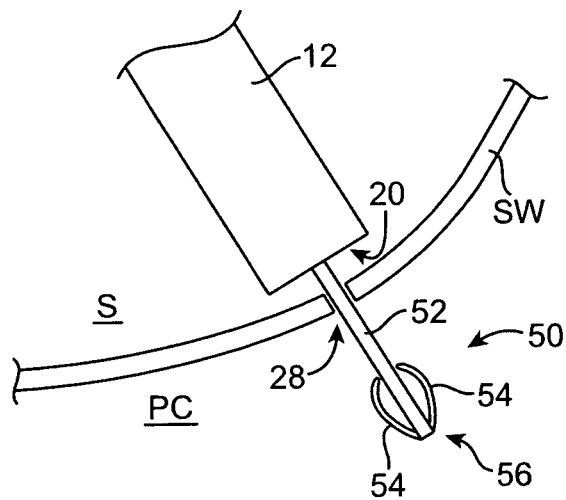
FIGS. 5A to 5E show yet another example for transgastric access utilizing an expandable tissue urging device deployable through a working lumen of the shapelock instrument.

In yet another variation for acquiring access to the peritoneal cavity PC, once gastric opening 28 has been formed, a tissue retraction instrument 50 may be passed through shapelock lumen 20 and through an un-dilated gastric opening 28 to pull the tissue surrounding gastric opening 28 over or onto elongate body 12. An example of such a tissue retraction instrument 50 is shown in FIG. 5A, which is seen having been advanced through gastric opening 28 with deployable retraction arm members 54 in a low-profile configuration where one or more arm members 54, e.g., at least two arm members, are retracted with respect to a flexible retraction shaft 52.

Figure 5B:
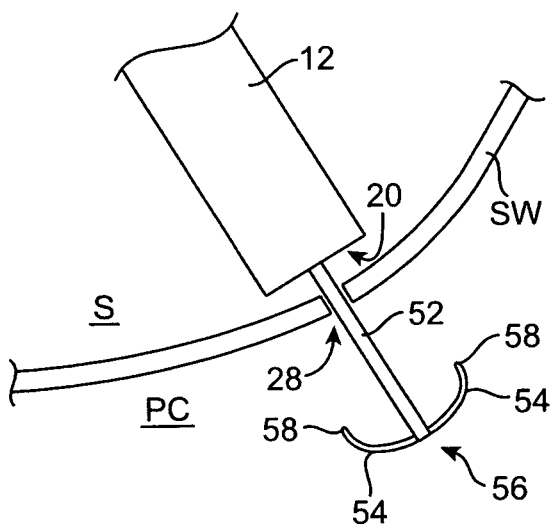

Retraction arm members 54 may be configured into a curved, arcuate, or otherwise angled member such that when pivoted or rotated about connection 56 at a distal end of retraction shaft 52, the distal ends 58 of retraction arm members 54 are curved or angled proximally towards elongate body 12 and a deployed diameter of retraction arm members 54 is equal to greater than a diameter of elongate body 12, as shown in FIG. 5B. Retraction arm members 54 may be fabricated from any number of materials which are biocompatible, e.g., stainless steel, Nitinol, high-density polymers, etc.

Figure 5C:
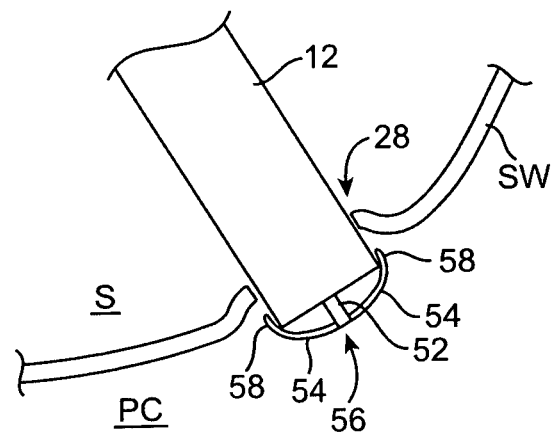
Figure 5D:
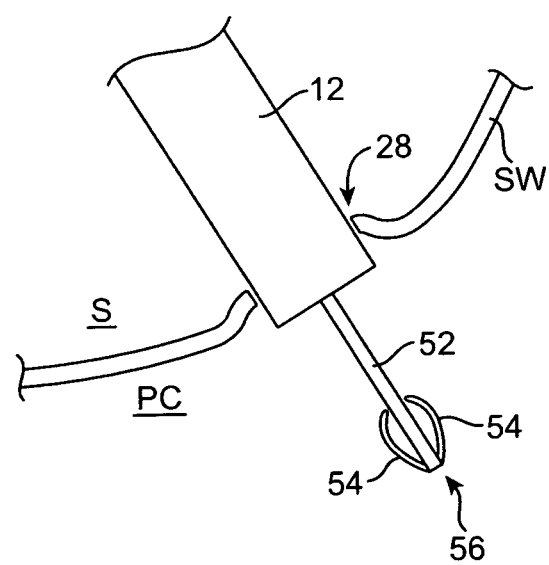
Figure 5E:
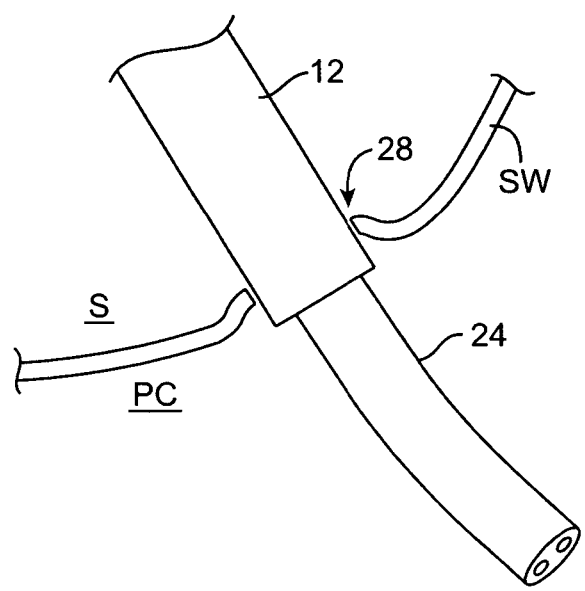

Once retraction arm members 54 are deployed or expanded, as in FIG. 5B, flexible retraction shaft 52 may be pulled proximally relative to elongate body 12 until the tissue surrounding gastric opening 28 is pulled over or onto elongate body 12 by the deployed distal ends 58 of retraction members 54, as shown in FIG. 5C. Alternatively, elongate body 12 may be pushed distally relative to deployed retraction members 54 until the surrounding tissue is pulled or pushed thereupon. Once the elongate body 12 is pushed through gastric opening 28, retraction shaft 52 may be pushed distally and retraction arms 54 reconfigured into its low-profile for proximal withdrawal through elongate body 12, as shown in FIG. 5D. Once retraction instrument 50 has been withdrawn, endoscope 24 may be advanced through elongate body 12 and further advanced into the peritoneal cavity PC, as shown in FIG. 5E.

Figure 6A:
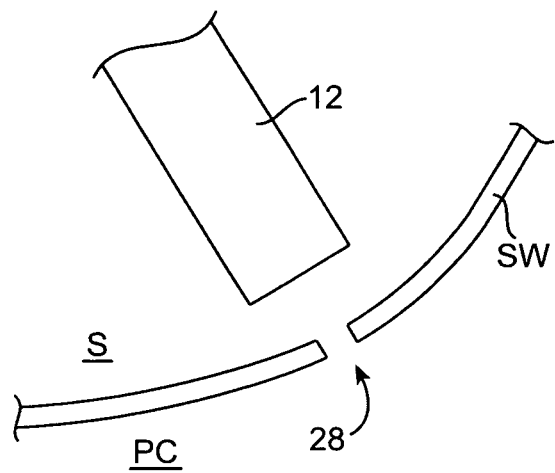
FIGS. 6A to 6F show yet another example for transgastric access utilizing a shapelock instrument having one or more reconfigurable members deployable from the shapelock instrument for pulling the instrument through the stomach tissue wall.
Figure 6B:
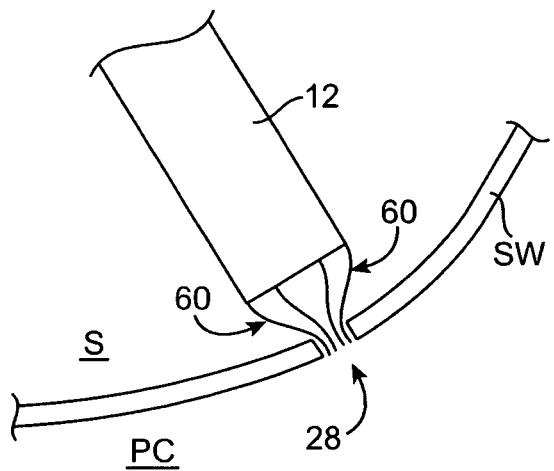

In yet another variation for accessing the peritoneal cavity PC from within the stomach S, elongate body 12 may be positioned adjacent to or against gastric opening 28 it a rigidized or flexible state, as described above and as shown in FIG. 6A. Once elongate body 12 has been desirably positioned, one or more deployable retraction members 60 may be projected from the distal end of elongate body 12. Retraction members 60 may be fabricated from a shape memory alloy, e.g., Nitinol, such that when positioned within its respective retraction member lumens 62, retraction members 60 are configured in a straightened shape for delivery. However, when first urged distally from elongate body 12, retraction members 60 may be biased to initially converge towards a longitudinal axis of the elongate body 12 to facilitate the initial insertion of the retraction members 60 into and through gastric opening 28, as shown in FIG. 6B.

Figure 6C:
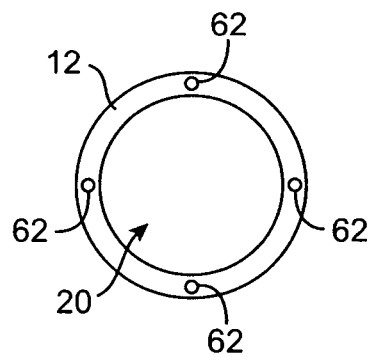
Figure 6D:
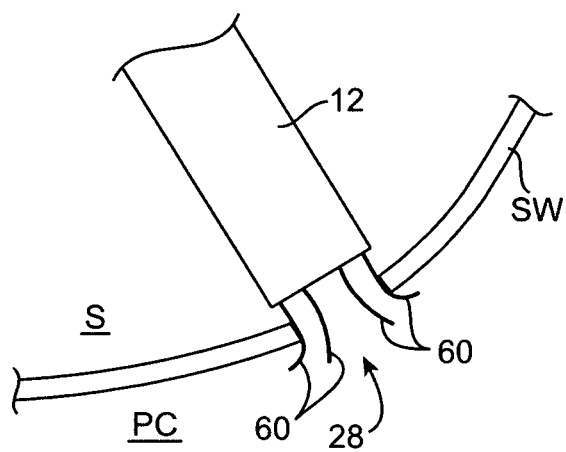

Retraction members 60 may be positioned about a circumference of the distal end of elongate body 12 in an asymmetric or uniform spacing. Moreover, any number of retraction members 60 may be utilized, e.g., two, three, four, or more as practicable, although four are shown in the end view of the example of FIG. 6C. As retraction members 60 are urged further distally from elongate body 12, they may be adapted to then reconfigure into a radially hooked or angled configuration extending away from the longitudinal axis of elongate body 12. As retraction members 60 begin to extend radially and outwardly, they may contact the tissue surrounding gastric opening 28 and begin dilating the opening 28, as shown in FIG. 6D. The further retraction members 60 are urged distally, the greater the hooked or angled configuration.

Figure 6E:
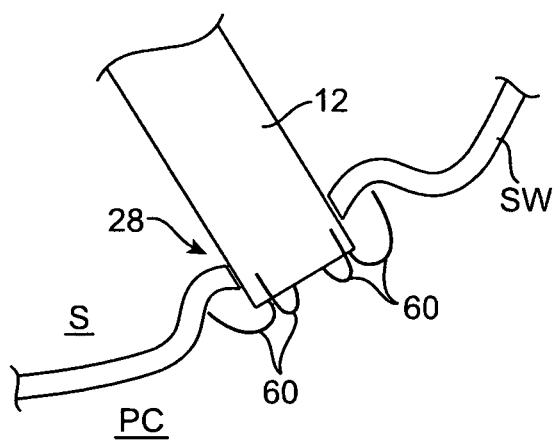
Figure 6F:
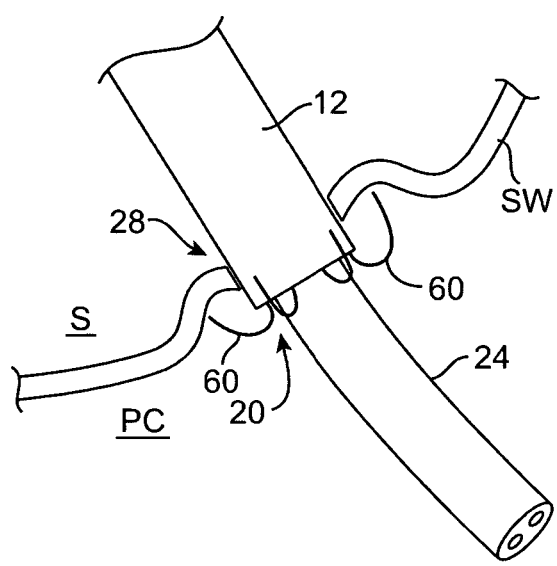

Accordingly, retraction members 60 may be urged until the retained surrounding tissue is pushed over or upon the outer surface of elongate body 12, as shown in FIG. 6E. Once the tissue around gastric opening 28 has been desirably pushed over elongate body 12, retraction members 60 may be withdrawn back into elongate body 12, which may then be further advanced into the peritoneal cavity PC. Alternatively, the position of elongate body 12 and retraction members 60 may be maintained through gastric opening 28 and the endoscope 24 may be advanced through shapelock lumen 20 and into the peritoneal cavity PC, as shown in FIG. 6F.

Figure 7A:
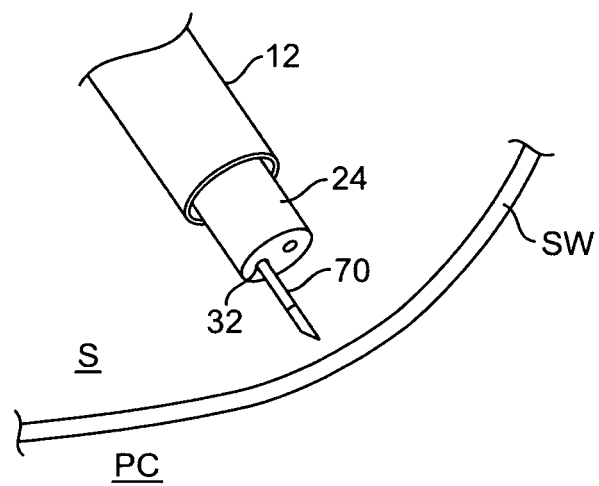

Another aspect of transgastric access may include adequate insufflation of the peritoneal cavity PC and/or stomach S during advancement of an instrument through the stomach wall SW. When advancing a needle knife or ablation tool through the stomach wall SW, the physician may risk inadvertently cutting or piercing into any number of body structures, e.g., the peritoneal and/or abdominal wall, liver, aortic artery, etc., adjacent to the stomach through which a gastric opening 28 is to be formed. Thus, one method for facilitating the safe incision through a stomach wall SW and into the peritoneal cavity PC may include the use of a flexible needle catheter or guidewire 70 which may be deliverable through the endoscopic working lumen 32, as shown in FIG. 7A.

Figure 7C:
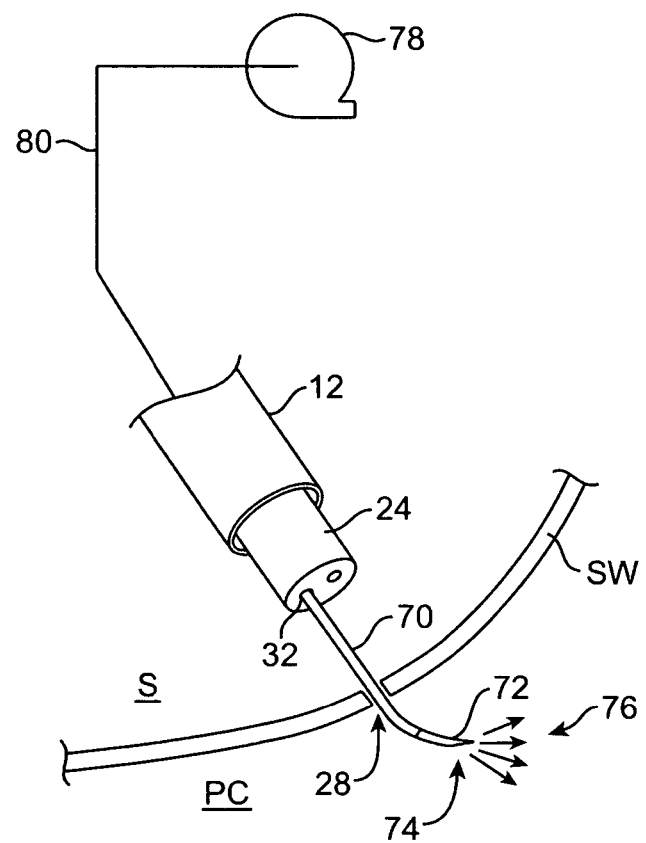

Flexible needle catheter or guidewire 70 may include a hollow catheter or hollow guidewire having a needle body 72 with a needle lumen 74 defined therethrough attached to the distal end of the catheter or guidewire. Alternatively, the distal end of the needle catheter 70 may be tapered into a piercing tip. As shown in FIG. 7B, the needle body 72 may be advanced distally out of elongate body 12 and/or endoscope 24 to pierce through the portion of the stomach wall SW to create gastric opening 28. Once needle body 72 has just pierced through the stomach wall SW, it may be advanced slowly into the peritoneal cavity PC and a fluid or gas 76, e.g., water, saline, carbon dioxide, nitrogen, air, etc., may be pumped into the peritoneal cavity PC to insufflate the region, e.g., $\leq 15$ mmHg and as shown in FIG. 7C, to lift adjacent body structures away from the external surface of the stomach wall SW. Accordingly, a pump 78 located external to the patient body may be fluidly connected via fluid line 80 through elongate body 12 to needle catheter or guidewire 70. Once the region surrounding gastric opening 28 has been sufficiently insufflated, a needle knife, ablation probe, or other instrument may be passed through gastric opening 28 or stomach wall SW without hitting any adjacent body structures.

Figure 8A:
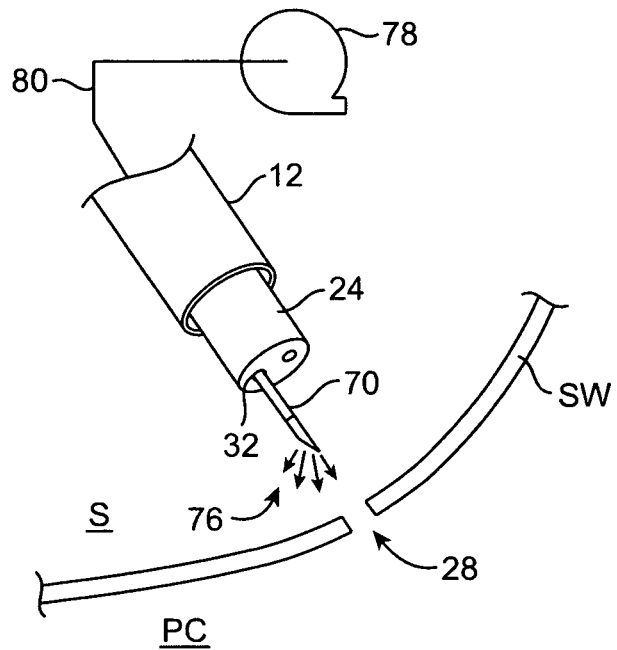
FIGS. 8A and 8B show the flexible catheter or guidewire device utilized to insufflate or re-insufflate the interior of the stomach.

Additionally or alternatively, needle catheter or guidewire 70 may be utilized to insufflate or re-insufflate the stomach S after a procedure has been performed within the peritoneal cavity PC, as shown in FIG. 8A. Once elongate body 12 and/or endoscope 24 are to be withdrawn from the peritoneal cavity PC, the stomach S may be in a deflated condition because of insufflation gas escaping through gastric opening 28 into the peritoneal cavity PC or back through the esophagus. Accordingly, once endoscope 24 has been withdrawn back into the stomach S, needle catheter or guidewire 70 may be deployed within the stomach S to insufflate or re-insufflate the stomach S so that the gastric opening 28 may be clearly visible for then closing the opening 28.

Figure 8B:
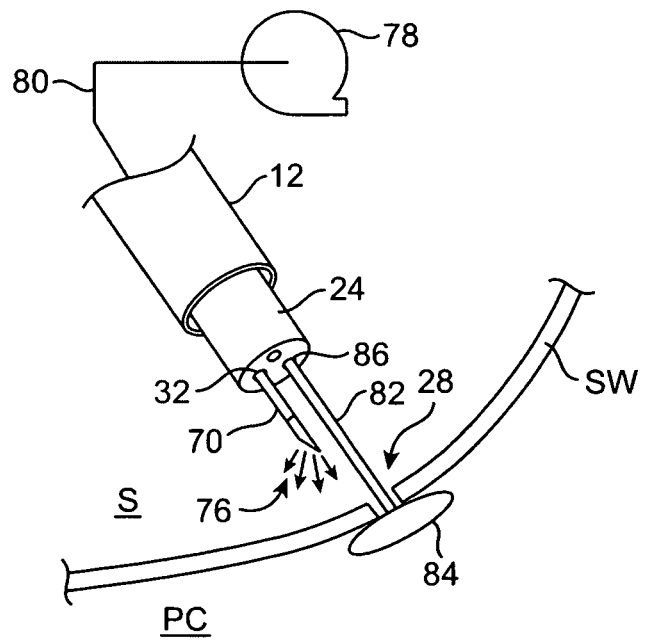

To facilitate the re-insufflation of the stomach S, gastric opening 28 may alternatively be sealed or plugged temporarily through a variety of apparatus, as described below in further detail. One example is shown in FIG. 8B which shows an inflatable balloon 84 advanced via inflation shaft 82 through an additional endoscopic lumen 86. Balloon 84 may be delivered via endoscopic lumen 86 in a deflated condition and passed through gastric opening 28. Balloon 84 may then be inflated to a size larger than gastric opening 28 and pulled against the exterior surface of stomach wall SW to plug or seal gastric opening 28. With opening 28 sealed temporarily, needle catheter or guidewire 70 may be used to insufflate the interior of the stomach S. After the stomach S has been sufficiently insufflated, i.e., insufflated such that visualization of the interior stomach wall SW is possible, the gastric opening 28 may be sealed and balloon 84 may be deflated and withdrawn proximally through gastric opening 28 before it is entirely sealed from the peritoneal cavity PC.

Figure 9:
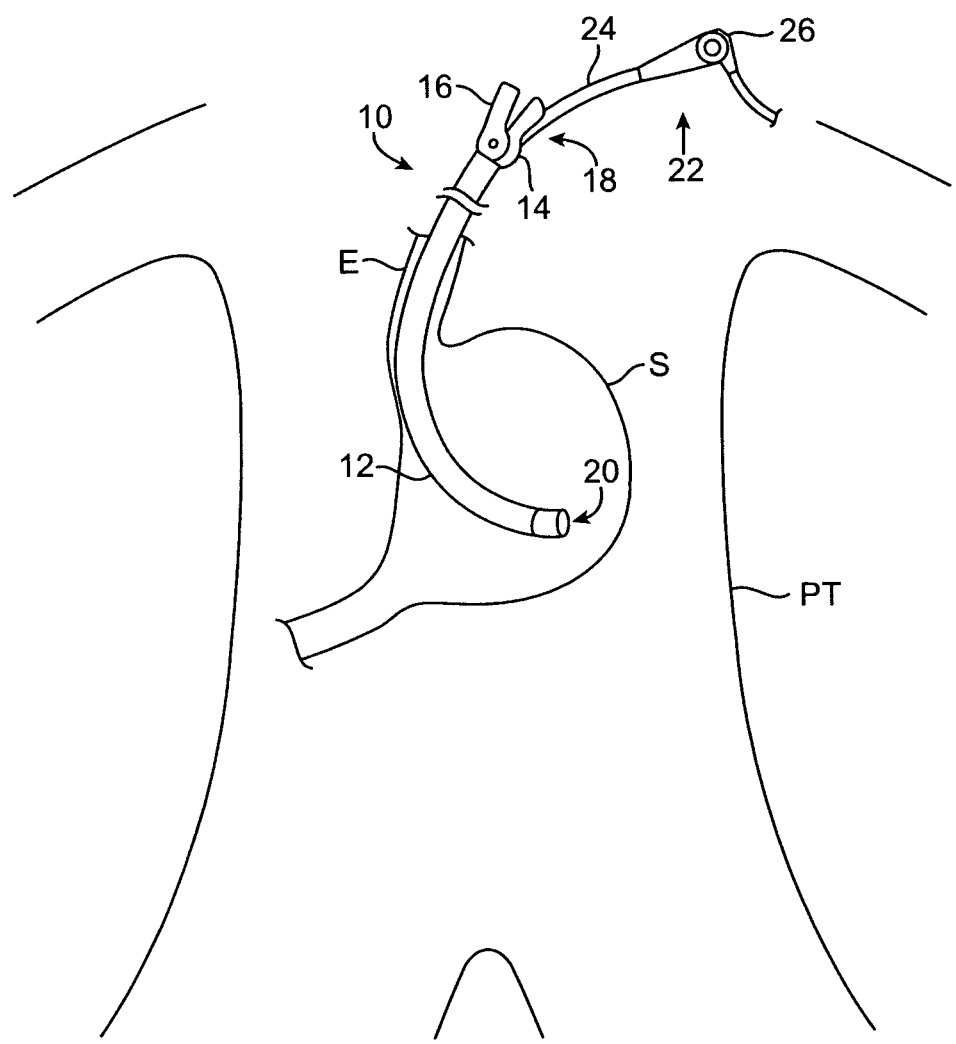
FIG. 9 shows the elongate body as having been advanced trans-esophageally into the patient's stomach and desirably positioned for transgastric advancement through the stomach wall.

In addition to endoluminal methods and devices, laparoscopic, trans-abdominal, and/or other percutaneous approaches and procedures may be utilized in combination with any of the above-described endoluminal approaches to facilitate intra-abdominal access within a patient body PT. Turning now to FIG. 9, elongate body 12 may be seen as having been advanced endoluminally, e.g., through the patient's mouth and esophagus E and into stomach S, until the opening or working lumen 20 has been desirably positioned within stomach S for transgastric advancement through the stomach wall.

As described above, an incision or gastrotomy may be made within the stomach wall and an endoscope, elongate body, or other instrument may be passed through or along elongate body 12, through the gastrotomy, and into the peritoneal cavity of the patient body PT. An instrument for making the incision and/or dilating the opening may be advanced through or along elongate body 12 for an endoluminal transgastric approach. Other variations may include utilizing trans-abdominal procedures in combination with a transgastric approach for obtaining intra-abdominal access.

Figure 10A:
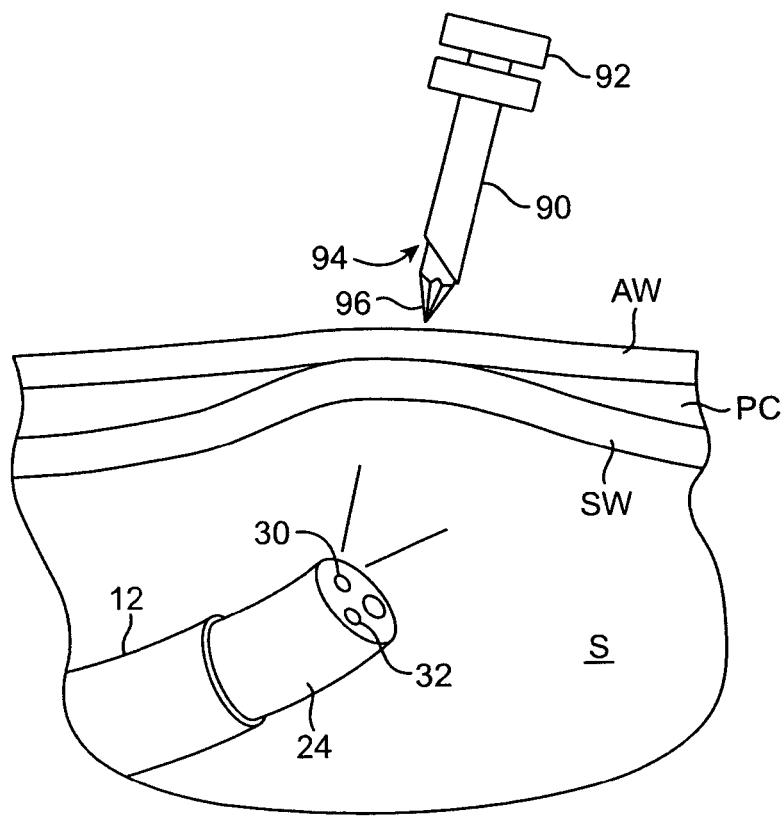
FIGS. 10A to 10D show an example of transgastric access through the stomach wall and into the peritoneal cavity facilitated by trans-abdominal access.
Figure 10B:
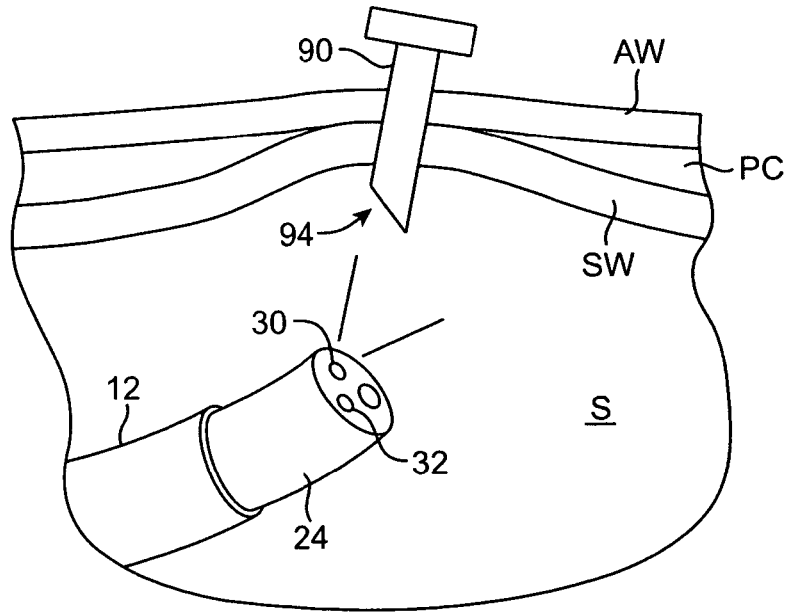

As shown in FIGS. 10A to 10D, transgastric access may be facilitated utilizing trans-abdominal procedures similar to those for placing gastrostomy tubes in a patient. A portion of the abdominal wall AW adjacent to the stomach S is illustrated in FIG. 10A with elongate body 12 and, e.g., endoscope 24, positioned within stomach S. Endoscope 24 may provide lighting via lumen 30 to illuminate the interior of stomach S and may also optionally provide insufflation through endoscope 24 or through another lumen. With stomach wall SW adjacent to a portion of abdominal wall AW, an access port such as trocar 90 with obturator 92 positioned through trocar lumen 94 may be advanced from outside the patient body and through abdominal wall AW, peritoneal cavity PC, and through stomach wall SW into stomach S, as shown in FIG. 10B.

Obturator 92 may be provided with a piercing tip 96 to facilitate its passage through the tissue into stomach S. Once the access port or trocar 90 has been pierced through stomach S, obturator 92 may be removed such that trocar lumen 94 is clear to provide unobstructed access. Trocar 90 may include seals or gaskets therewithin to maintain insufflation patency. The light provided by lumen 30 transmitted through abdominal wall AW may be generally seen from within stomach S and externally of the patient body. During placement of the access port, the light provided through lumen 30 may be utilized as an indicator to the physician that access to stomach S is clear of any intervening organs or tissue body and the trocar 90 may be advanced through the abdominal wall without inadvertently injuring surrounding tissue.

Figure 10C:
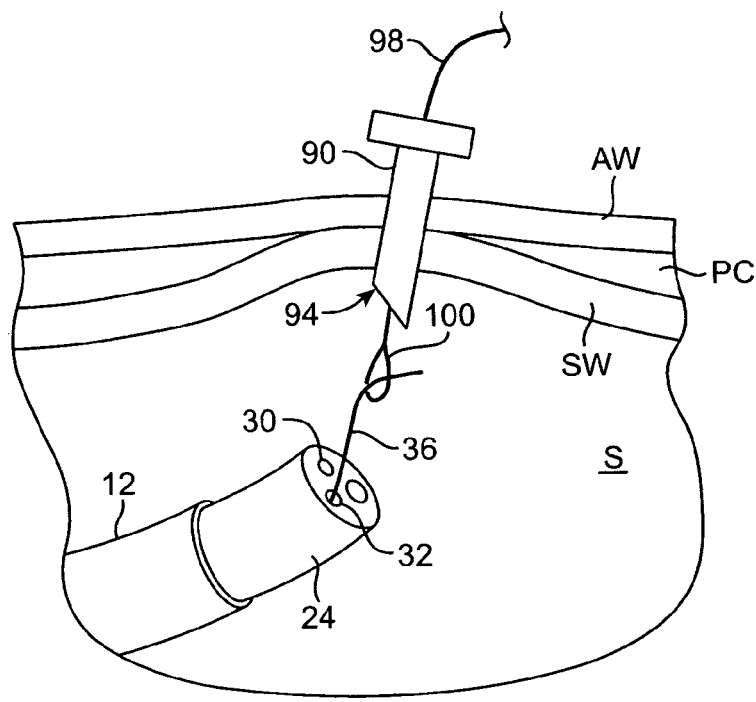
Figure 10D:
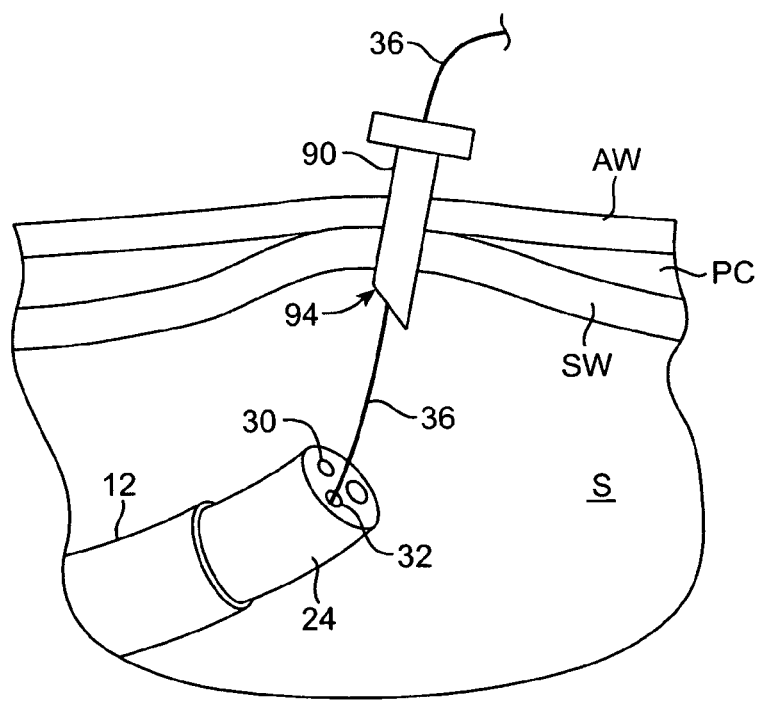

With trocar 90 in place, a guidewire 36 may be optionally advanced into stomach S through lumen 32 of endoscope 24 or through another working lumen defined through or along elongate body 12. Prior to, during, or after guidewire 36 has been positioned within stomach S, a snare or other retrieval device 98 may also be advanced through trocar lumen 94 from outside the patient body and into stomach S where the snare or, e.g., loop 100, may be manipulated to grasp, snare, or otherwise hold guidewire 36, as shown in FIG. 10C. Retrieval device 98 may be then withdrawn proximally through trocar lumen 94 while pulling guidewire 36 from within stomach S to outside the patient body, as shown in FIG. 10D.

Figure 11A:
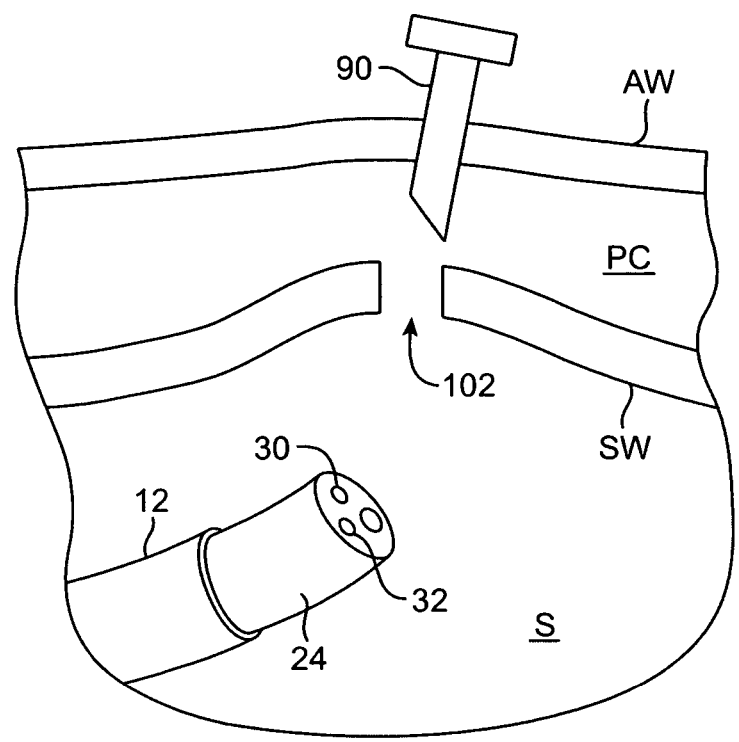
FIG. 11A shows a portion of the stomach wall released or otherwise dislodged from a trocar leaving a gastrotomy or opening in the stomach wall.

With guidewire 36 routed from the patient's mouth, through stomach S, and back outside the patient body through stomach wall SW and abdominal wall AW, any number of instruments, e.g., dilation instruments for dilating the opening in the stomach wall SW, may be guided into the stomach S or into peritoneal cavity PC via trocar lumen 94 along guidewire 36. Alternatively, guidewire 36 may be omitted entirely so that once trocar 90 has been advanced through the abdominal wall AW and stomach wall SW, trocar 90 may be proximally withdrawn until stomach wall SW is released or otherwise dislodged from trocar 90 leaving gastrotomy or opening 102, as shown in FIG. 11A.

Additionally or alternatively, a grasping instrument may be endoluminally advanced through or along elongate body 12 or endoscope 24 and articulated to pull stomach wall SW free from trocar 90. Elongate body 12 may be rigidized during such a procedure to provide for instrument stability. Moreover, the insufflation in stomach S, if utilized, may be reduced at least temporarily such that the stomach wall SW is relaxed and not taut. Once stomach wall SW is free from trocar 90, elongate body 12 and/or endoscope 24, or any other endoluminally advanced instrument, may be advanced through opening 102, as described above. Moreover, additional instruments, e.g., laparoscopic instruments, may be passed through trocar 90 for assisting passage of elongate body 12, endoscope 24, or other instruments through opening 102. Other instruments may be passed through trocar 90 for facilitating procedures within the patient's peritoneal cavity PC and/or for closing the opening 102 (or multiple openings) from outside stomach S once a procedure is completed and any endoluminal instruments have been withdrawn proximally through opening 102.

Figure 11B:
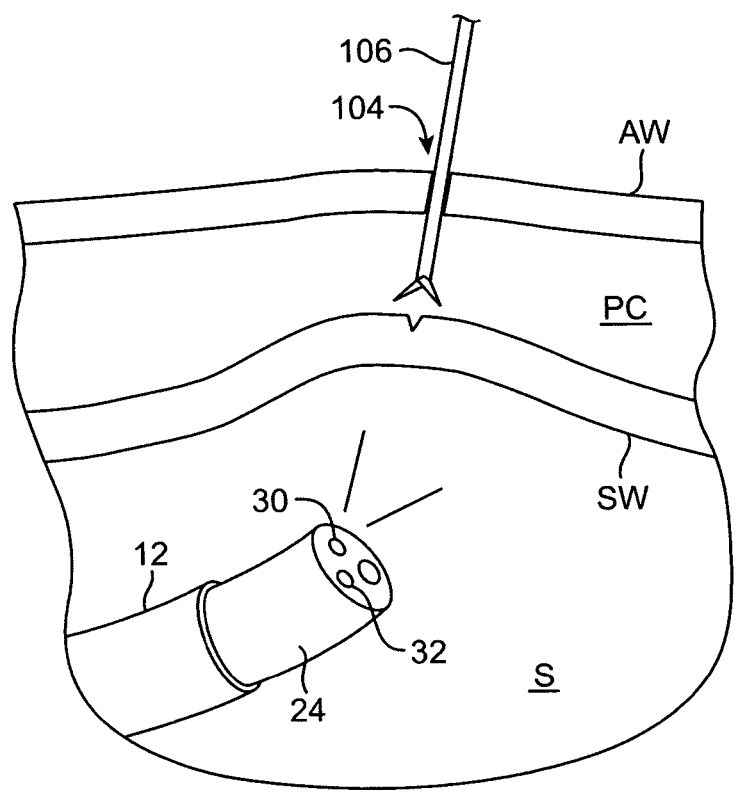
FIG. 11B shows an incising instrument passed through a simple abdominal incision from outside the patient body to assist in creating a gastrotomy or opening in the stomach wall.

As shown in FIG. 11B, rather than utilizing a trocar 90 or other access port for creating openings within the stomach wall SW through the patient's abdominal wall AW, a simple incision 104 may be created in the abdominal wall AW of the patient and an incising instrument 106, such as an ablation probe, electrocautery catheter, needle knife, scissors, etc., may be passed through the incision from outside the patient body and directed towards an exterior surface of stomach wall SW to cut, ablate, or otherwise create an opening therethrough to provide transgastric access for endoluminally delivered instruments. This eliminates the need for endoluminal delivery and manipulation of any elongate incising instrument through or along elongate body 12 or endoscope 24. Once the incision in stomach wall SW has been made, instrument 106 may be withdrawn from the patient body and incision 104 in abdominal wall AW may be closed before, during, or after completion of an endoluminal procedure within the peritoneal cavity PC.

Figure 12:
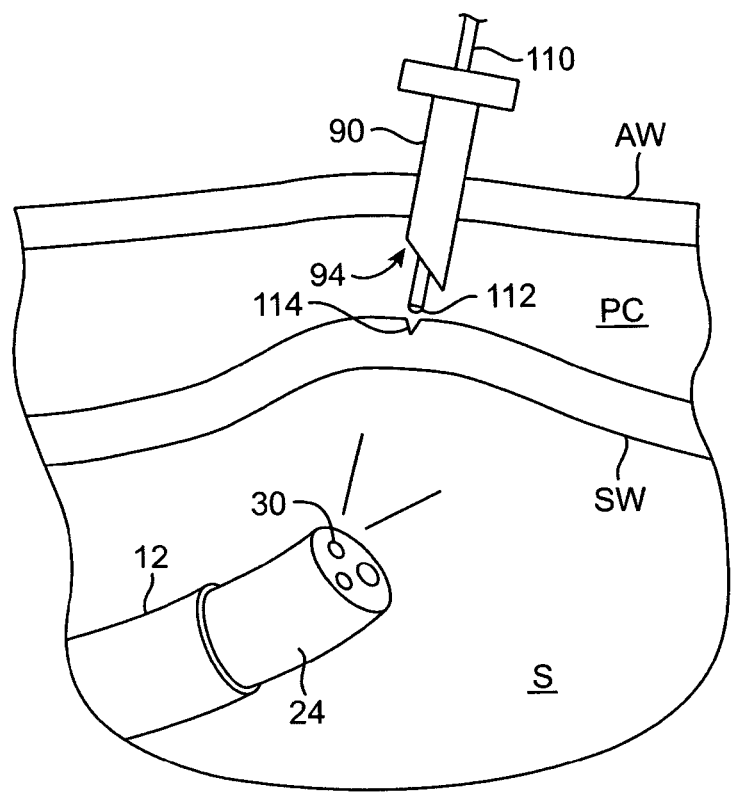
FIGS. 12 and 13 illustrate other variations of creating incisions through the stomach wall by the insertion of incising instruments through the abdominal wall from outside the patient body.
Figure 13:
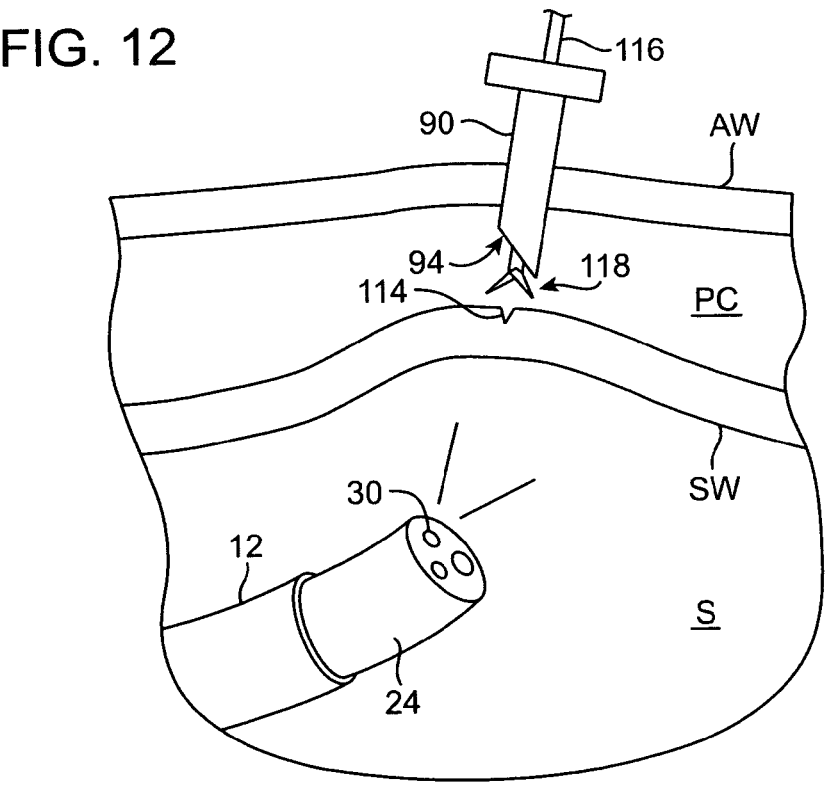

FIGS. 12 and 13 illustrate other variations of creating incisions through the stomach wall SW by the insertion of incising instruments through the abdominal wall AW from outside the patient body. In this case, trocar 90 or other access ports may be utilized rather than passing tools directly through an incision in the abdominal wall AW. FIG. 12 illustrates an example in which an ablation probe 110, e.g., electrocautery catheter, needle knife, etc., having an energizable probe tip 112 may be passed through trocar lumen 94 to create an incision 114 through stomach wall SW from the exterior surface. Lumen 30 may be used to illuminate a portion of the stomach wall SW from within the stomach S to act as a guide for locating where incision 114 may be placed along stomach wall SW.

Moreover, endoscope 24 may also be used to provide endoluminal visualization while incision 114 is made. Alternatively, a laparoscope or other visualization instrument may be provided through trocar 90 or another abdominal incision to provide additional or alternative visualization through the abdominal wall AW. FIG. 13 shows a similar variation utilizing a mechanical incising instrument 116 passed through trocar 90 where the incising instrument 116 has an articulatable cutting end effector 118, e.g., laparoscopic scissors.

Figure 14A:
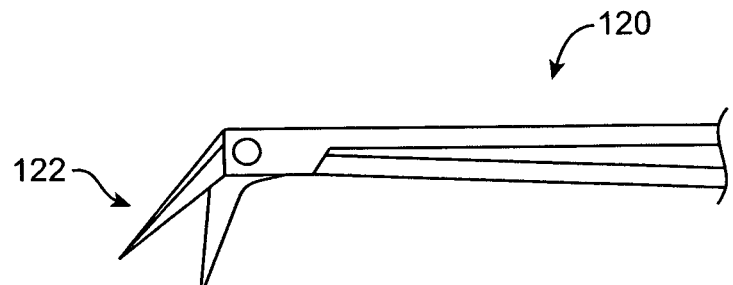
FIGS. 14A to 14D show other examples of incising instruments which may be advanced through the abdominal wall either directly through an incision or through a trocar or other access port.
Figure 14B:
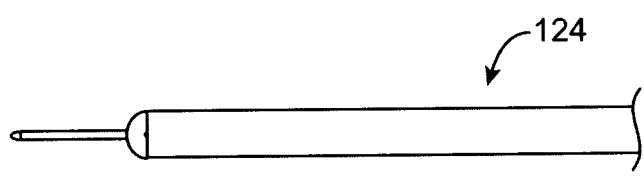
Figure 14C:
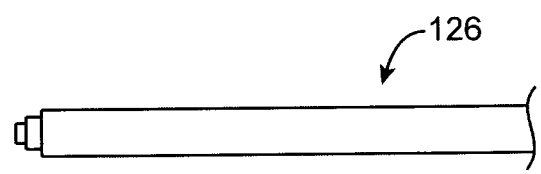
Figure 14D:
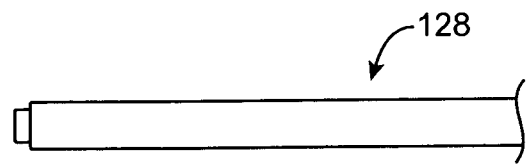

Other examples of incising instruments which may be advanced through the abdominal wall AW either directly through an incision or through a trocar 90 or other access port are shown in FIGS. 14A to 14D. FIG. 14A illustrates a pair of scissors, such as a pair of Potts-Smith scissors 120 having cutting jaws 122. FIG. 14B shows a needle knife 124 while FIG. 14C illustrates an RF probe 126 and FIG. 14D illustrates a laser probe 128. These instruments, as well as other incising instruments disclosed herein, are not intended to be limiting but are shown as examples of types of incising tools which may be utilized to effectuate transgastric incisions.

Figure 15A:
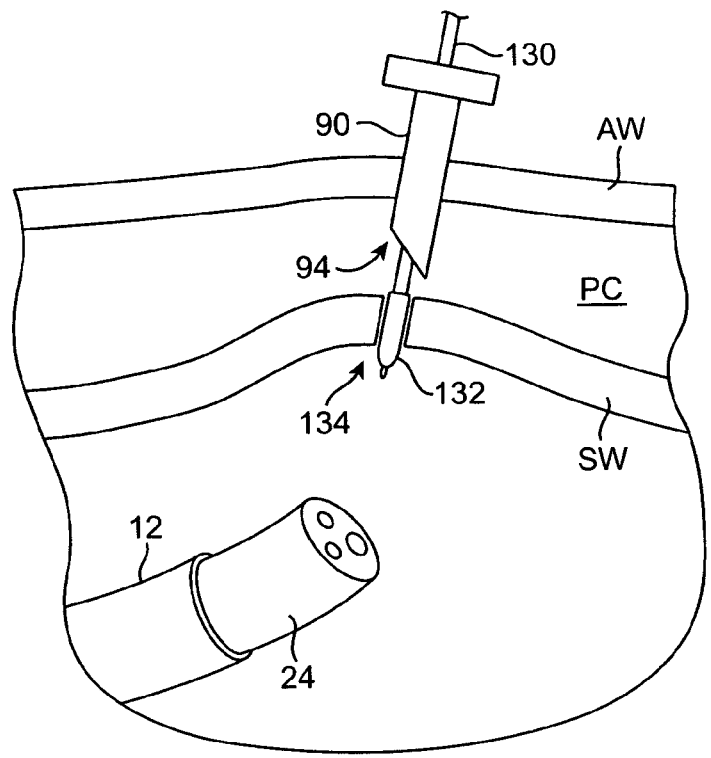
FIGS. 15A and 15B show an example in which a dilation balloon assembly may be passed through an abdominal incision and into the gastric opening to dilate the opening for facilitating passage of instruments into the peritoneal cavity from within the stomach.

Once an incision has been made in the stomach wall SW, it may be desirable to dilate the opening prior to passing the endoscope 24 or elongate body 12 through the stomach wall SW and into the peritoneal cavity PC. An example for endoluminally dilating the opening is described above in FIGS. 2C and 2D utilizing a dilation balloon delivered trans-esophageally. In this example, a dilation balloon assembly 130 may be passed through trocar lumen 94 (or directly through an incision in the abdominal wall AW) such that a dilation balloon in its deflated state 132 is positioned within an undilated opening 134, as shown in FIG. 15A.

Figure 15B:
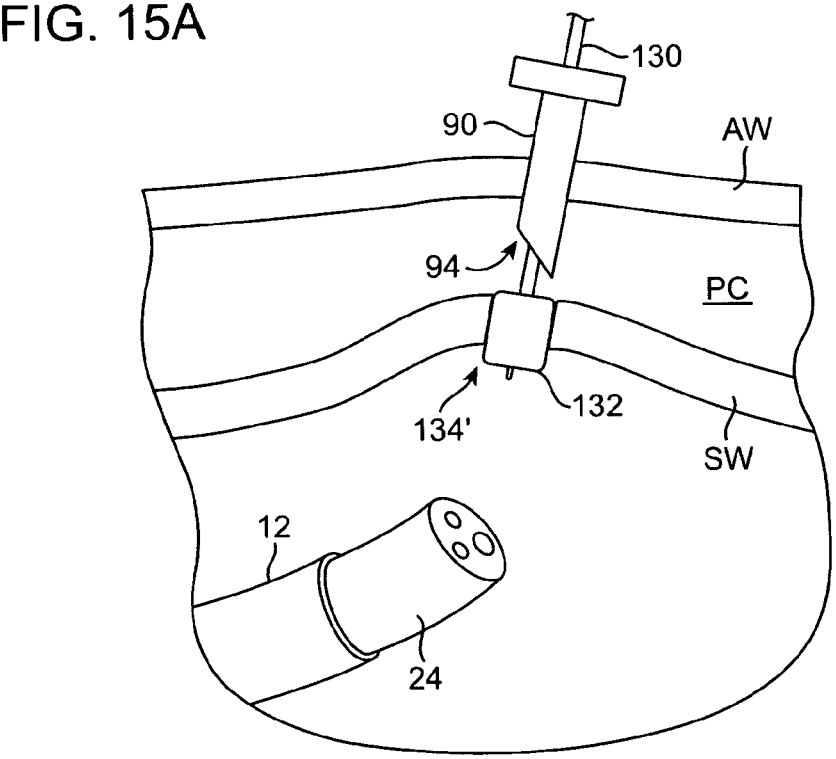

Placement of balloon 132 within opening 134 may be accomplished under visualization provided by endoscope 24 or alternatively through a laparoscope positioned within another opening through the abdominal wall AW, if so desired. Additionally, dilation balloon assembly 130 may be passed over a guidewire 36 (if optionally utilized and as shown above in FIG. 10D) to facilitate the positioning of balloon assembly 130 within the undilated opening 134. Once balloon 134 is in position within opening 134, the balloon may be expanded to its inflated state 132' to thereby dilate opening 134', as shown in FIG. 15B.

Figure 16:
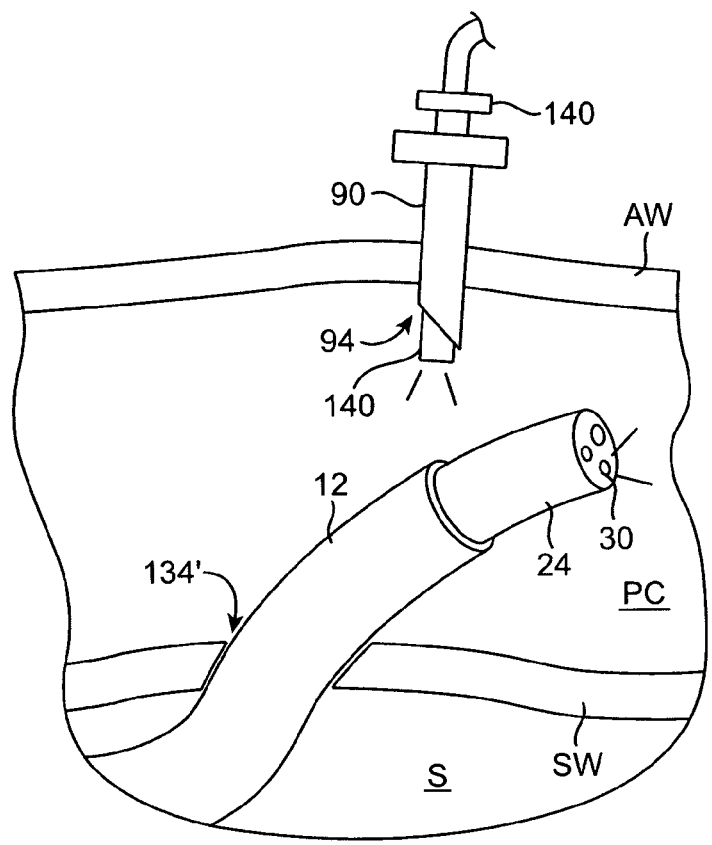
FIG. 16 shows an example of a laparoscope positioned through a trocar lumen to provide for laparoscopic imaging of a procedure within the peritoneal cavity.
Figure 17:
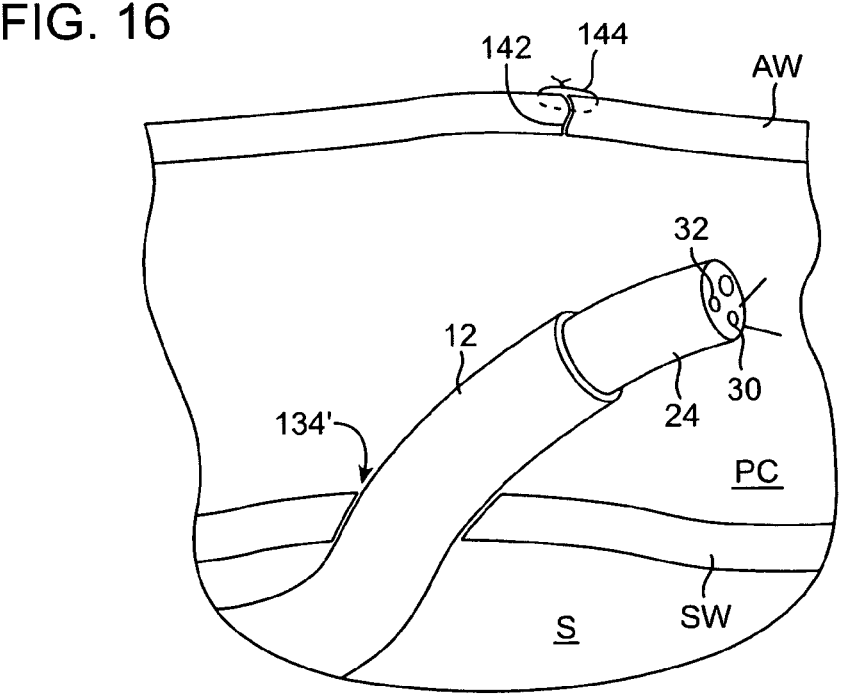
FIG. 17 shows another example where visualization is provided via an endoscope once an abdominal incision has been closed.

As mentioned above, visualization of the procedure may be provided or facilitated through the abdominal opening by placing an imager through the abdominal wall AW proximate to the gastric opening. For example, as shown in FIG. 16, laparoscope 140 may be positioned through trocar lumen 94 to provide for laparoscopic imaging of the procedure. The images provided from laparoscope 140 may be utilized alone or in combination with the images provided through endoscope 24. Alternatively, once the gastric opening has been made, any instruments or trocars 90 may be removed from the abdominal incision 142, which may then be closed by any variety of wound closure fasteners 144, e.g., sutures, staples, clips, etc. In this case, visualization is provided by the endoscope 24, as shown in FIG. 17.

Figure 18A:
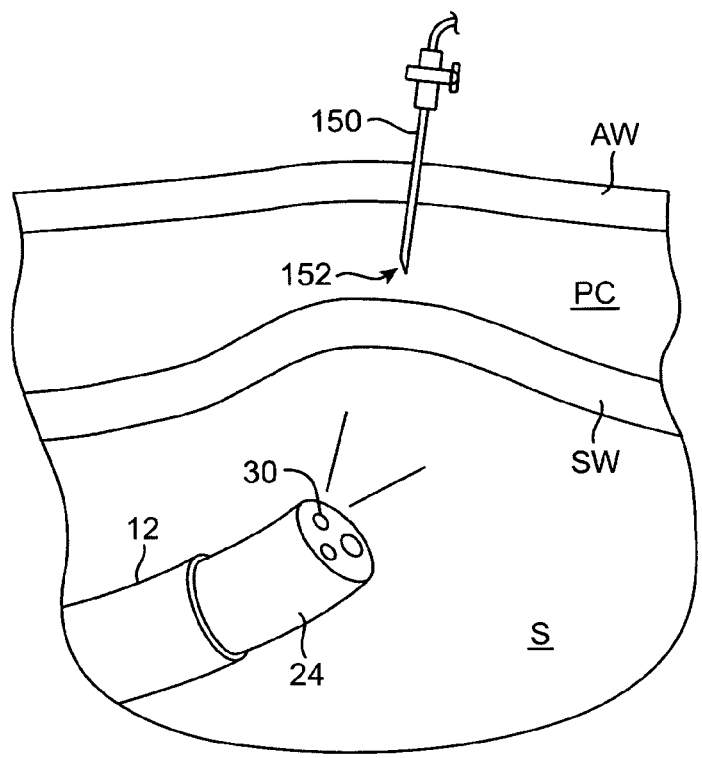
FIGS. 18A and 18B illustrate other access ports which may be utilized such as a Verres needle having a needle lumen inserted through the abdominal wall.
Figure 18B:
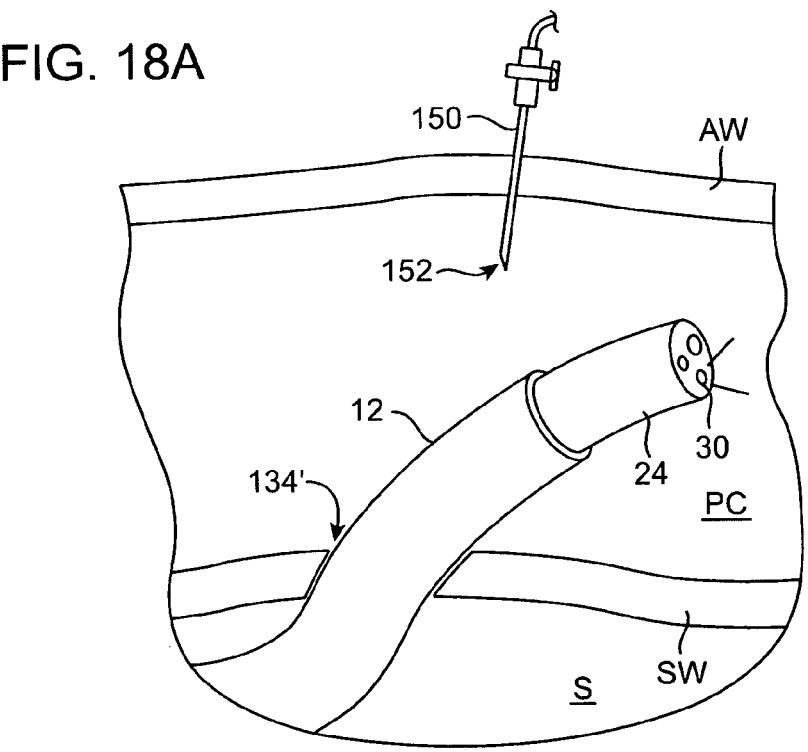

Trocar 90 may be utilized as an access port or instruments may be simply passed from outside the patient body and through abdominal incisions to provide access to the exterior of the stomach wall SW. Other access ports which may be utilized may include hollow needles, e.g., Verres needle 150 having a needle lumen 152, which may be inserted through the abdominal wall AW to provide for prior peritoneal insufflation, as shown in FIG. 18A. Verres needle 150 may be inserted before inserting a trocar through the abdominal wall AW or prior to passing elongate body 12, endoscope 24, or any other instruments through the gastric opening 134' and into the peritoneal cavity PC, as shown in FIG. 18B. Additionally, once Verres needle 150 has been placed through the abdominal wall AW, an incising probe, energized and/or tapered, may be inserted directly through the needle lumen 152 for creating an incision from the stomach exterior and through the stomach wall SW, which may be dilated endoluminally from within the stomach S utilizing any of the methods and devices described above.

Figure 19:
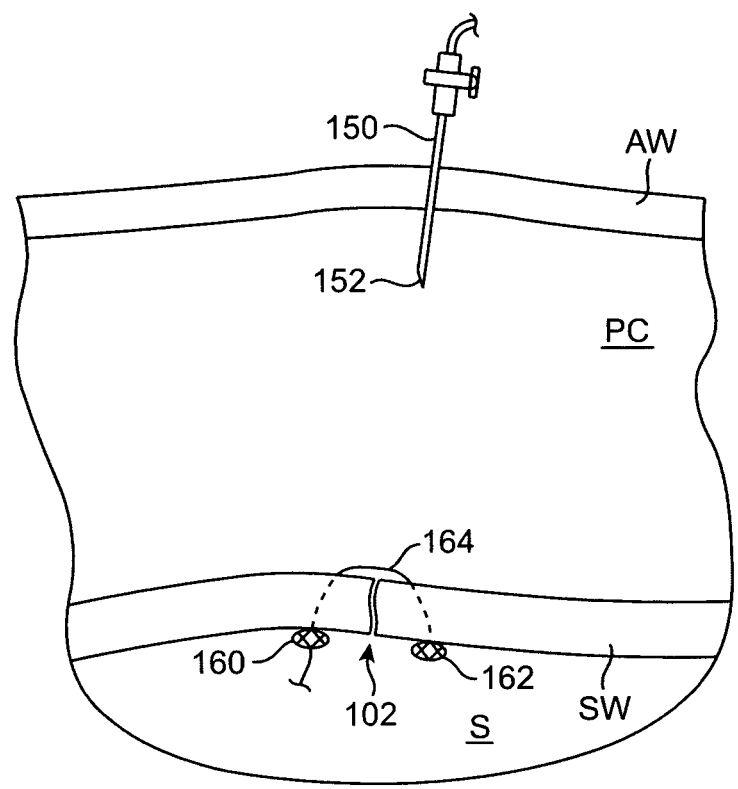
FIG. 19 shows tissue anchors which have been deployed endoluminally from within the stomach to approximate the edges of the gastric opening.

After a procedure has been accomplished within the peritoneal cavity PC, the devices and/or instruments may be withdrawn proximally through the gastric opening 102. Opening 102 may then be closed to seal stomach wall SW utilizing, e.g., tissue anchors 160, 162 slidably connected via a connecting member such as suture 164. Tissue anchors 160, 162 may be deployed endoluminally from within stomach S to approximate the edges of opening 102, as shown in FIG. 19 and as described in further detail below.

Turning now to closure of wounds and openings, such as gastrotomies, utilizing endoluminal instruments and methods, various examples are described below. Although the examples and illustrations below describe the use of a shapelockable or rigidizable body, the methods and instruments described below may also be utilized with flexible endoscopes for wound closure.

Figure 20A:
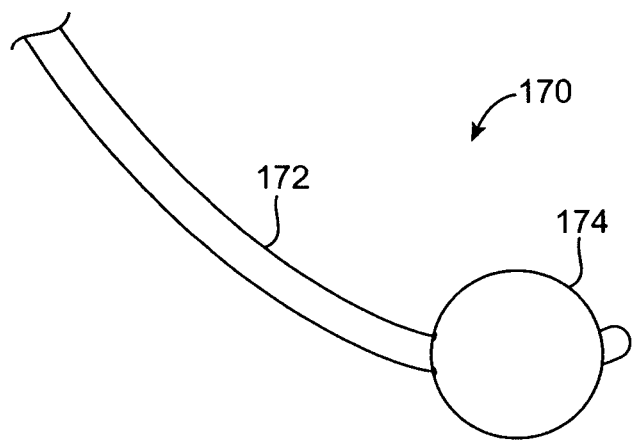
FIGS. 20A and 20B show variations of tissue markers having an elongate flexible body with an inflatable member reconfigurable between a low-profile advancement configuration and an expanded marking configuration.
Figure 20B:
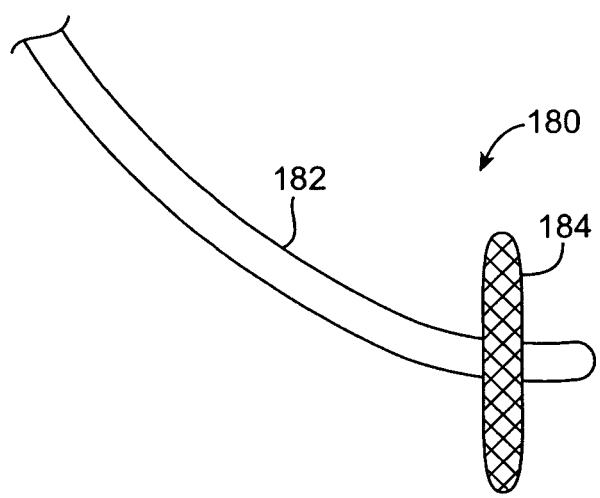

Once gastric opening 28 is made in the gastric tissue wall, as shown above, the opening 28 may be closed through a variety of endoluminal apparatus and methods. However, maintaining the location of the opening 28 along the stomach wall may be desirable once the elongate body 12 has been removed from the opening 28 to facilitate the closure of the opening 28 after the procedure has been completed within the peritoneal space. As shown in FIGS. 20A and 20B, variations of tissue markers are illustrated. FIG. 20A shows one example of marker assembly 170 having an elongate flexible body 172 with an inflatable balloon member 174 reconfigurable between a low-profile advancement configuration and an expanded marking configuration. The inflatable member may have an expanded diameter which is larger than that of the elongate body 12 and which is also larger than the opening 28. FIG. 20B likewise shows another example of marker assembly 180 having elongate flexible body 182 with a reconfigurable mesh member 184 which may also be reconfigured from a low-profile advancement configuration to an expanded tissue marking configuration. Although these examples illustrate balloon and mesh variations, these are intended to be merely illustrative and are not intended to be limiting. Other examples of expandable members as generally known within the art are intended to be within the scope of this disclosure.

Figure 21:
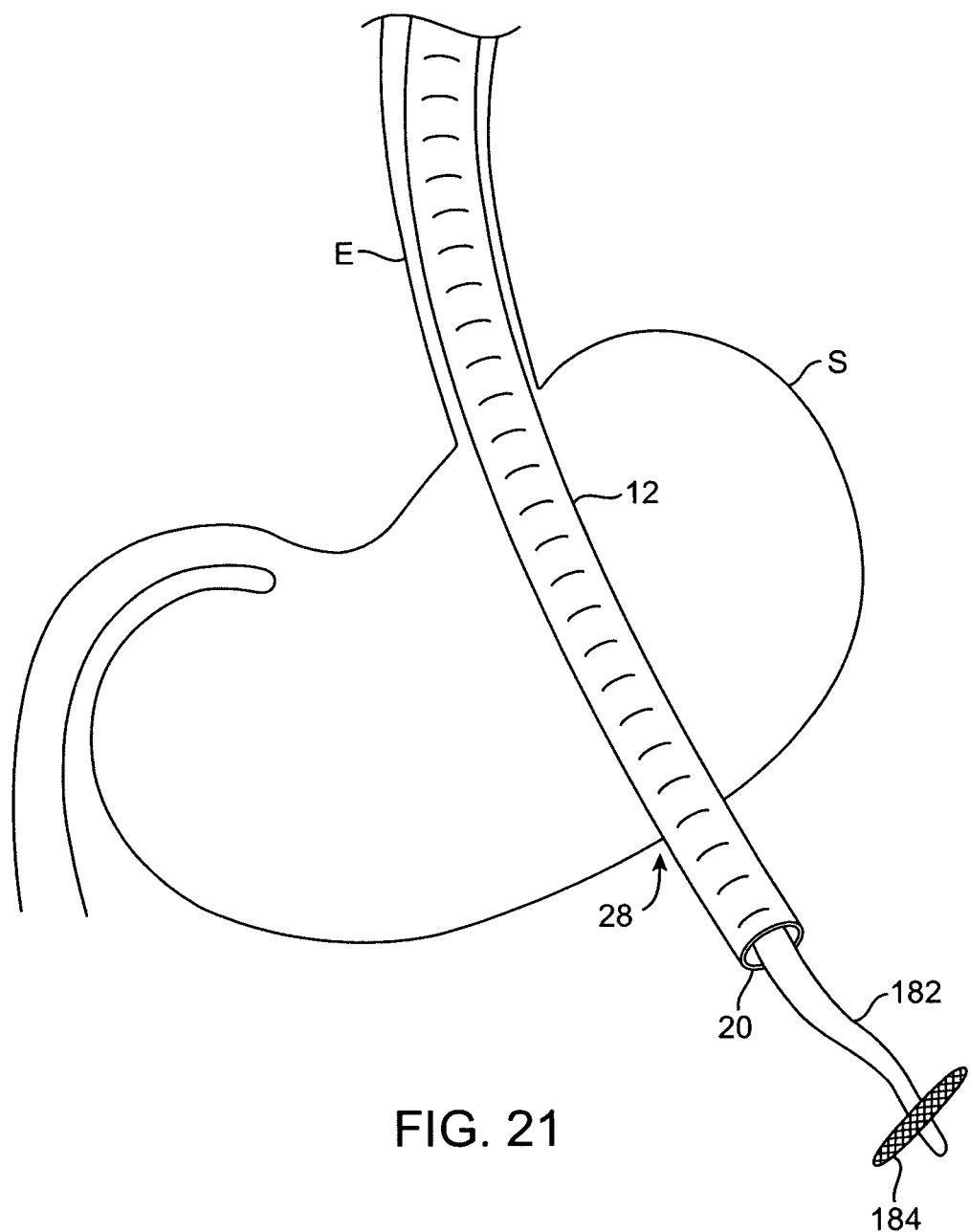
FIGS. 21 to 24 illustrate one example for advancing an elongate body trans-esophageally into and through a stomach and deployment of a tissue marking assembly for marking or indicating an opening made within the tissue wall.
Figure 22:
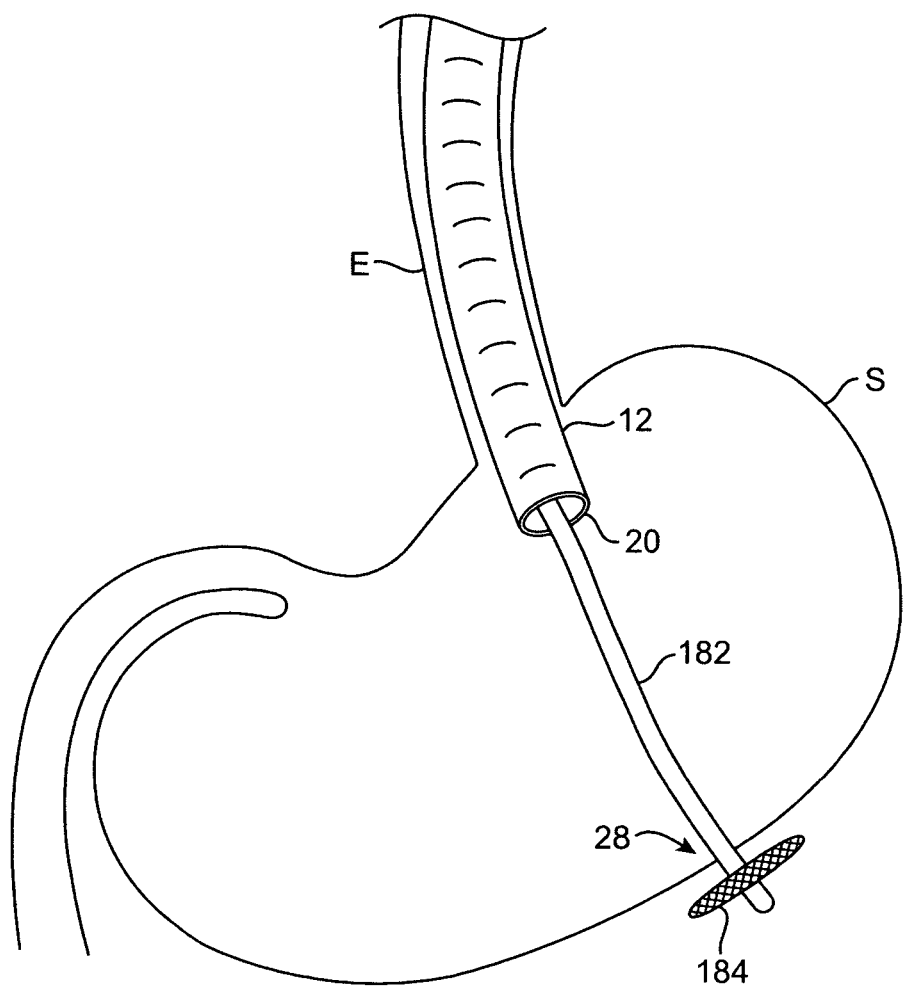

In use, as shown in FIG. 21, prior to withdrawing elongate body 12 from opening 28 along the stomach wall, elongate flexible body 182 and, e.g., mesh member 184, may be advanced through shapelock lumen 20 into the peritoneal cavity PC. Once mesh member 184 has been sufficiently advanced past the lumen opening, mesh member 184 may be expanded. With mesh member 184 now in its expanded shape, flexible member 182 may optionally be withdrawn proximally until mesh member 184 is resting against the outer serosal tissue layer of stomach S, as shown in FIG. 22. The expanded profile prevents the pulling of mesh member 184 proximally back through opening 28 and may now serve as a marker for easily locating the position of opening 28.

Figure 23:
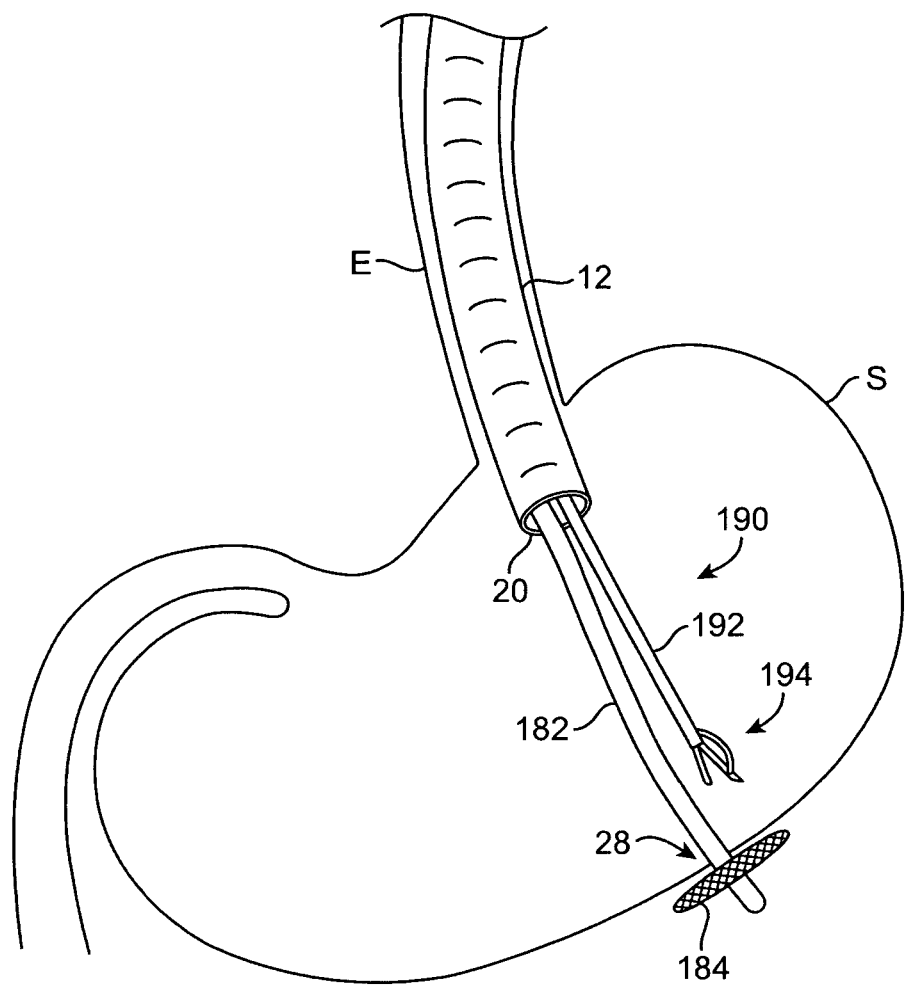

Once opening 28 has been marked with mesh member 184 and flexible body 182 extending therethrough, a tissue approximation and securement assembly 190 may be advanced through elongate body 12 and into the stomach S, as shown in FIG. 23. Assembly 190 may be advanced optionally through the esophagus E as a separate instrument externally of elongate body 12, if so desired. Tissue approximation and securement assembly 190 may include a flexible body 192 and a tissue manipulation and securement end effector 194 for grasping, manipulating, and/or otherwise securing regions of tissue. Examples of assembly 190 may be seen in further detail in U.S. patent application Ser. No. 10/955,245 filed Sep. 29, 2004 and Ser. No. 11/070,863 filed Mar. 1, 2005, each of which is incorporated herein by reference in its entirety.

Using assembly 190, opening 28 may be closed and secured by deploying one or more tissue anchors 200, 202 connected via a length of suture 204, as mentioned above. Anchors 200, 202 may be configured to be cinched unidirectionally towards one another as disclosed in further detail in U.S. patent application Ser. No. 10/840,950 filed May 7, 2004, which is incorporated herein by reference in its entirety. Further details are also disclosed for deploying tissue anchors and closing openings 28 along the gastric tissue in U.S. patent application Ser. No. 10/918,217 filed Aug. 11, 2004, which is incorporated above by reference. Reconfigurable "basket"-type anchors generally comprise a number of configurable struts or legs extending between at least two collars or support members. Other variations of these or other types of anchors are also contemplated for use in an anchor locking or cinching assembly. The basket anchors may comprise various configurations suitable for implantation within a body lumen. Basket anchors are preferably reconfigurable from a low profile delivery configuration to a radially expanded deployment configuration in which a number of struts, arms, or mesh elements may radially extend once released from a launch tube or needle. The basket anchor may have a number of reconfigurable struts or arm members extending between a distal collar and a proximal collar.

Figure 24:
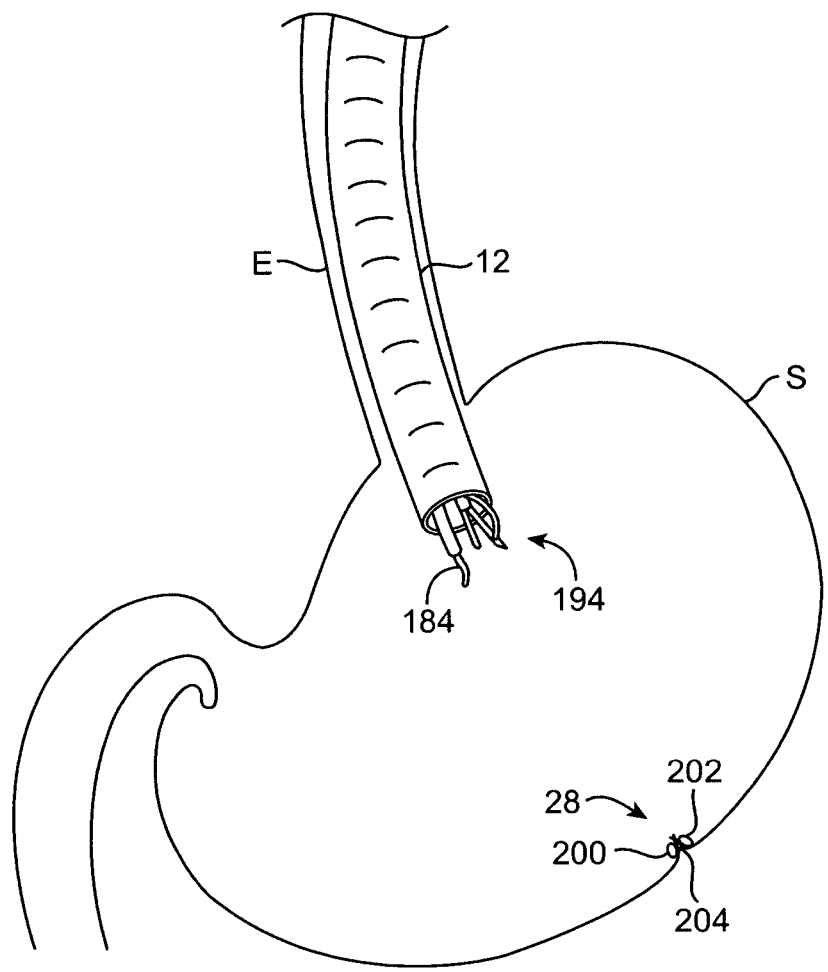

With the marker in place distally of opening 28, mesh member 184 may be used as a platform for facilitating the grasping and manipulating of the overlying tissue against mesh member 184 by assembly 190. Once tissue anchors 200, 202 have been deployed adjacent to opening 28, mesh member 184 may be reconfigured into its low-profile configuration and withdrawn proximally back into the stomach S through opening 28 via flexible body 182. The tissue anchors may then be cinched or approximated towards one another to thereby close the opening 28, as shown in FIG. 24. Elongate body 12 may then be withdrawn from stomach S entirely or further procedures may be affected.

Figure 25A:
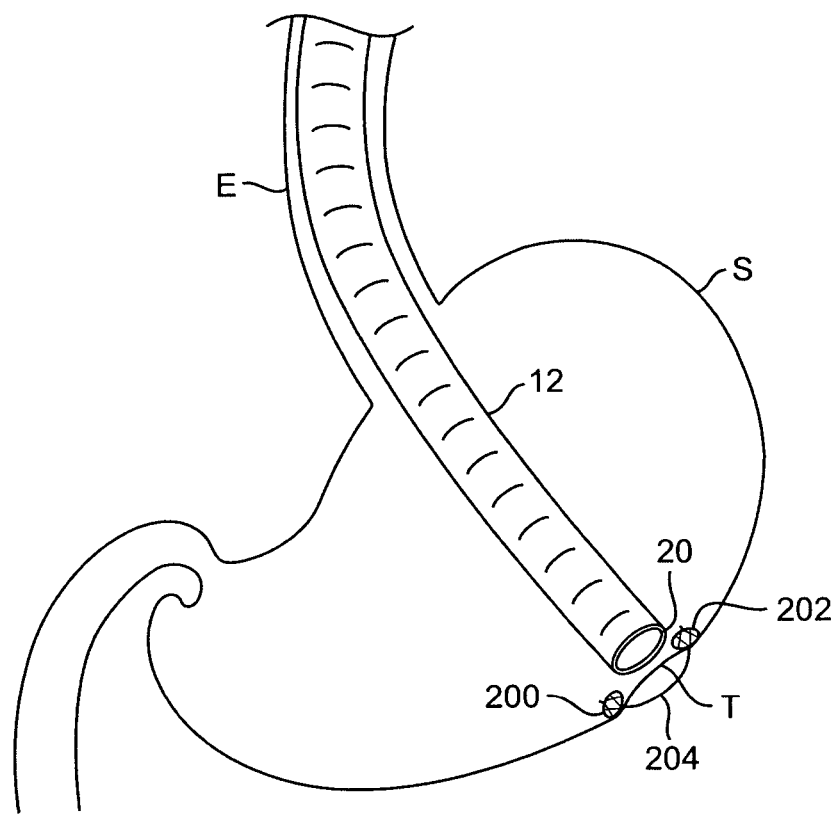
FIG. 25A shows another variation for deploying an anchor assembly for marking or otherwise indicating a location along the stomach wall prior to piercing and/or advancing an elongate body therethrough.

In an alternative method, elongate body 12 may be advanced into the stomach S and positioned adjacent to a tissue region of interest T through which the elongate body 12 and/or tools are to be advanced through and into the peritoneal cavity. Prior to piercing and/or dilating an opening along the stomach wall, tissue anchors 200, 202 interconnected via suture 204 may be deployed along the tissue region of interest T utilizing assembly 190, as described above, and as shown in FIG. 25A. With the tissue area marked by the deployed tissue anchors 200, 202, the lumen opening 20 of elongate body 12 may be repositioned or advanced against and/or through the tissue region T and an opening 28 may be formed or dilated in the tissue adjacent or proximate to anchors 200, 202.

Figure 25B:
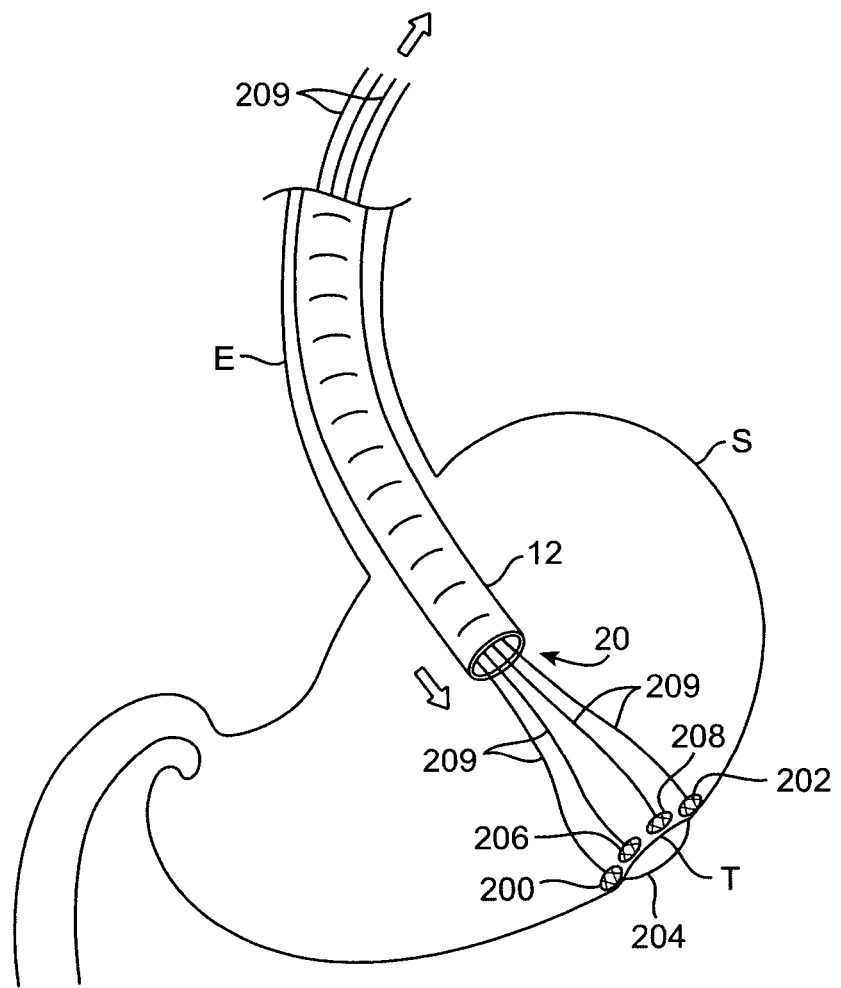
FIGS. 25B and 25C show an example where multiple pairs of tissue anchors may be deployed about the tissue region with their respective suture lengths leading from the tissue anchors proximally through the lumen or along the elongate body to outside the patient body.
Figure 25C:
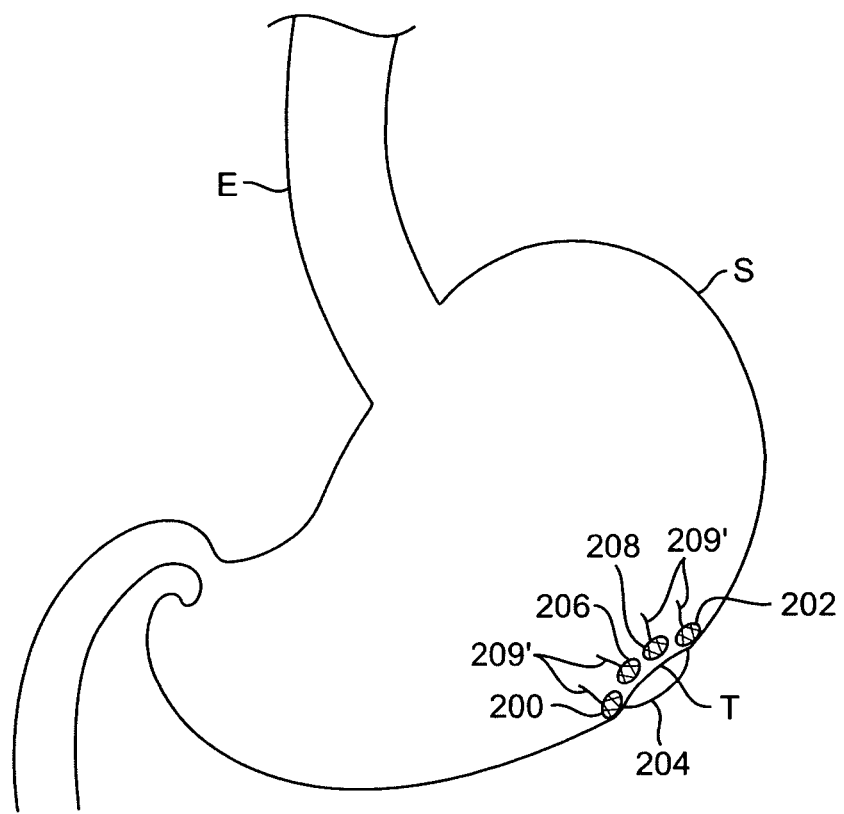

In an alternative variation for cinching the tissue anchors, FIG. 25B shows an example where, e.g., multiple pairs of tissue anchors 200, 202, 206, 208, may be deployed about the tissue region T with their respective suture lengths 209 leading from the tissue anchors proximally through lumen 20 or along elongate body 12 to outside the patient body. With the proximal ends of suture lengths 209 outside the patient's body, the suture 209 may be tensioned proximally while elongate body 12, in its rigidized state, may be urged distally against the tissue region. This counter-acting force can enable the tissue anchors 200, 202, 206, 208 to cinch towards one another to close any gastric openings by localizing forces between the distal end of elongate body 12 against the stomach tissue and the tissue anchors 200, 202, 206, 208. Once the tissue has been desirably approximated between the respective tissue anchors 200, 202, 206, 208, the suture may be cut 209' to release the anchors and the elongate body 12 may be removed from the stomach S, as shown in FIG. 25C.

After any procedures within the peritoneal space have been completed, any instruments and elongate body 12 may be withdrawn proximally through the opening 28, as mentioned. The opening 28 may be subsequently located within the stomach S by the position of anchors 200, 202 in the tissue and the opening 28 may then be easily closed by simply approximating the pre-deployed anchors towards one another.

Figure 26A:
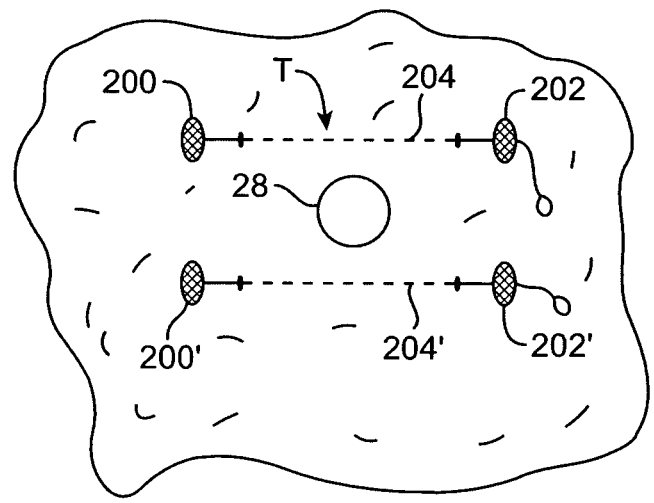
FIGS. 26A to 26C show examples for deploying the anchor assemblies for marking or indicating a location of the opening along the gastric wall.
Figure 26B:
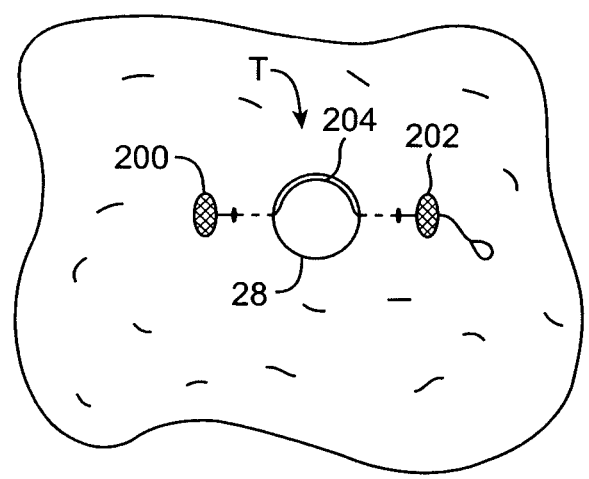

FIGS. 26A and 26B show two examples for the pre-deployment of tissue anchors 200, 202 relative to opening 28, which may be formed prior to or after deployment of the anchors within the tissue region T. In the example shown in FIG. 26A, a first set of tissue anchors 200, 202 connected via suture 204 may be deployed in the tissue region T and a second set of tissue anchors 200', 202' connected via suture 204' may also be deployed in the tissue region T at a distance from the first set of tissue anchors 200, 202. If opening 28 were made prior to deployment of the tissue anchors, the first and second sets of anchors may be deployed adjacently on either side of opening 28. If opening 28 were to be made after deployment of the tissue anchors, the first and second set of anchors may be deployed from one another at a distance sufficient to allow for the passage of elongate body 12 between the anchors without interference therefrom.

Figure 26C:
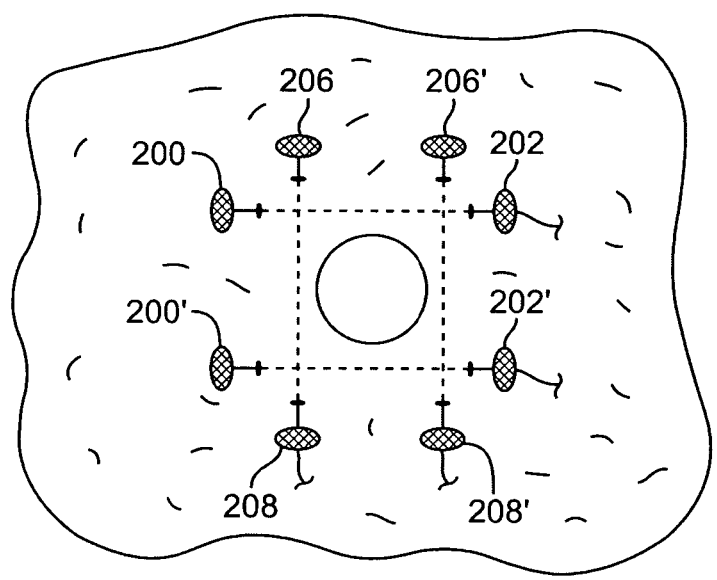

In another example as shown in FIG. 26B, opening 28 may be formed directly between tissue anchors 200, 202. If elongate body 12 is advanced through opening 28, suture 204 connecting tissue anchors 200, 202 may simply be pushed aside towards the edge of opening 28. FIG. 26C shows yet another example where multiple pairs of tissue anchors may be utilized about the tissue opening, e.g., in addition to anchor pairs 200, 202 and 200', 202', additional anchor pairs 206, 208 and 206', 208' may be utilized in a crossing pattern.

Figure 27A:
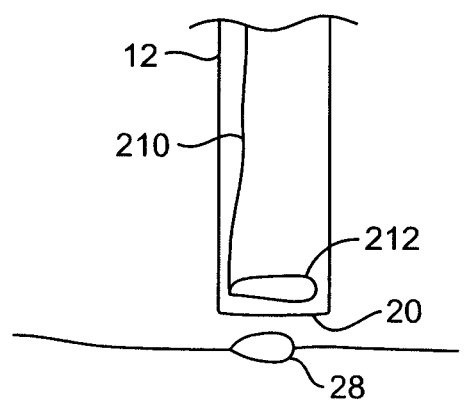
FIGS. 27A and 27B show another example for closing an opening within the gastric wall by drawing a region of tissue having the opening within a snare positioned around an opening of the elongate body.
Figure 27B:
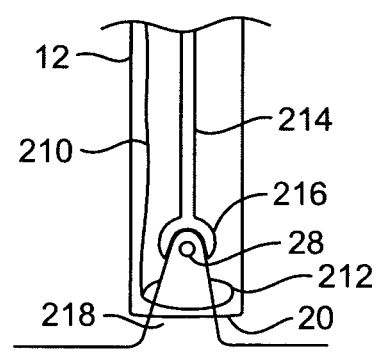

In yet another example for closing opening 28 of the stomach wall, FIGS. 27A and 27B show another variation where elongate body 12 may have a wire, cable, or suture 210 disposed within a lumen along the length of elongate body 12 and a snare or loop 212 connected to suture 210 positioned around the lumen opening 20 of elongate body 12. To close opening 28, in this example, a portion of tissue 218 having opening 28 defined therein may be drawn within elongate body 12 and through snare 212 via grasper 216 disposed at a distal end of elongate member 214. Once tissue portion 218 has been sufficiently drawn within elongate body 12, snare 212 may be actuated via suture 210 to be drawn upon and tighten over tissue 218 to thereby close opening 28, as shown in FIG. 27B.

Figure 28:
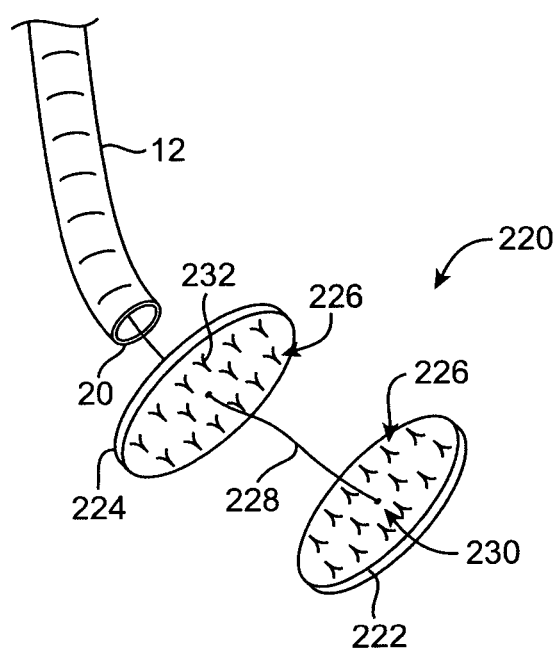
FIG. 28 shows yet another example of opposable substrates having a plurality of barbs therebetween for sandwiching a region of tissue having the opening.

In yet another variation shown in FIG. 28, a tissue closure assembly 220 may be delivered through elongate body 12 and ejected from shapelock lumen opening 20 to close a tissue opening. Closure assembly 220 may be comprised of a distal substrate 222 having a plurality of barbs or hooks 226 disposed over its surface. A suture or wire 228 may be connected to the distal substrate 222 at a location 230. A proximal substrate 224 may also have a plurality of barbs or hooks 226 disposed over its surface with suture or wire 228 also passing through the substrate 224 at a location 232. Barbs or hooks 226 may be defined along the surfaces of their respective substrates 222, 224 which face one another when suture 228 is tightened. Moreover, substrates 222, 224 are accordingly sized to correspond to one another and are made from a flexible material, e.g., polymeric, polyurethane, etc., such that they may be rolled or otherwise folded into elongate body 12 for endoluminal advancement through the patient body.

In use, when opening 28 is to be closed, distal substrate 222 may be ejected distally of opening 28 and allowed to expand. Once fully expanded, suture or wire 228 may be tightened to pull barbs or hooks 226 against the outer serosal layer of stomach tissue. Elongate body 12 may be pulled into stomach S and proximal substrate 224 may likewise be ejected and allowed to expand. With suture or wire 228 tightened, proximal substrate 224 may be urged against the inner mucosal layer of stomach tissue and into apposition against the distal substrate 222 to thereby sandwich the gastric tissue and opening 28 therebetween. Once desirably positioned, suture or wire 228 may be cut to leave the closure assembly 220 covering the opening 28 within stomach S.

Figure 29:
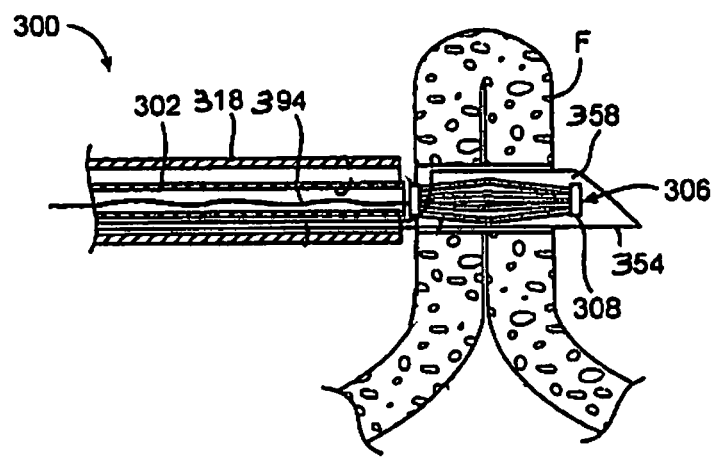
FIG. 29 shows a cross-sectional side view of an anchor delivery system delivering a basket-type anchor into or through a tissue plication.

FIG. 29 shows anchor delivery system 300 in proximity to tissue fold F. Again, tissue fold F may be disposed within a gastrointestinal lumen, such as the stomach, where tissue wall W may define the outer or serosal layer of the stomach. Delivery push tube or catheter 302 may be disposed within launch tube 318 proximally of basket anchor 306, which is shown in a compressed delivery configuration with a relatively low profile when disposed within needle lumen 358 of needle 354. A single basket anchor 306 is shown disposed within needle 354 only for illustrative purposes and is not intended to be limited by the number of basket anchors; rather, any number of basket anchors may be disposed within needle lumen 358 as practicable depending upon the desired procedure and anchoring results.

Figure 30:
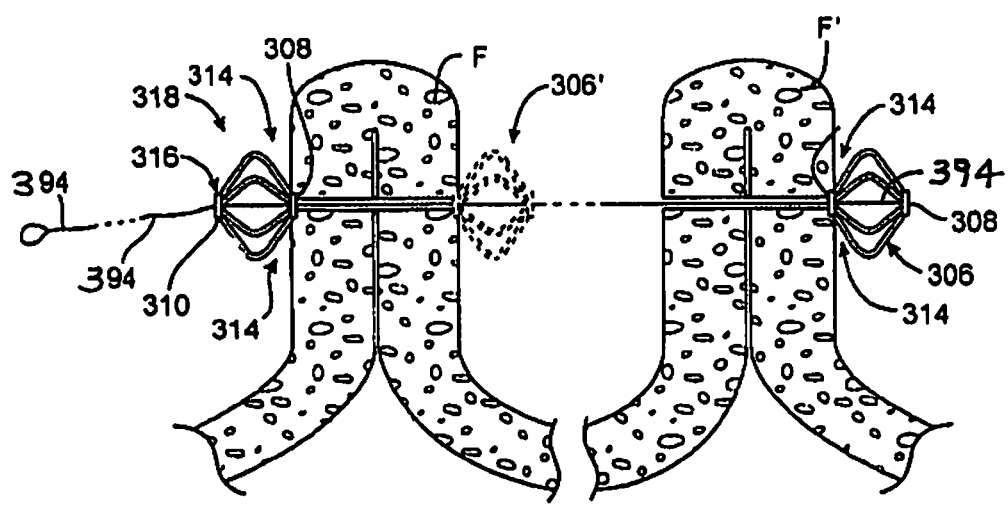
FIG. 30 shows a cross-sectional side view of multiple tissue plications which may be cinched towards one another and basket anchors as being deliverable through one or both tissue plications.

FIG. 30 shows one variation where a single fold F may be secured using basket anchor 306'. As seen, basket anchor 306' has been urged or ejected from needle 354 and is shown in its radially expanded profile for placement against the tissue surface. In such a case, a terminal end of suture 394 may be anchored within the distal collar of anchor 306' and routed through tissue fold F and through, or at least partially through, proximal anchor 318, where suture 394 may be cinched or locked proximally of, within, or at proximal anchor 318 via any number of cinching mechanisms 316 described herein. Proximal anchor 318 is also shown in a radially expanded profile contacting tissue fold F along tissue contact region 314. Locking or cinching of suture 394 proximally of proximal anchor 318 enables the adequate securement of tissue fold F.

If additional tissue folds are plicated for securement, distal basket anchor 306 may be disposed distally of at least one additional tissue fold F', as shown in FIG. 30, while proximal anchor 318 may be disposed proximally of tissue fold F. As above, suture 394 may be similarly affixed within distal anchor 306 and routed through proximal anchor 318, where suture 394 may be cinched or locked via proximal anchor 318, as necessary. If tissue folds F and F' are to be positioned into apposition with one another, distal basket anchor 306 and proximal anchor 318 may be approximated towards one another. As described above, proximal anchor 318 is preferably configured to allow suture 394 to pass freely therethrough during the anchor approximation. However, proximal anchor 318 is also preferably configured to prevent or inhibit the reverse translation of suture 394 through proximal anchor 318 by enabling uni-directional travel of anchor 318 over suture 394. This cinching feature thereby allows for the automated locking of anchors 306, 318 relative to one another during anchor approximation.

Although various illustrative embodiments are described above, it will be evident to one skilled in the art that various changes and modifications are within the scope of the invention. Moreover, such changes, modifications, and combinations of various features from different embodiments, as practicable, are intended to be included within the scope of this disclosure. It is further intended in the appended claims to cover all such changes, modifications, and combinations that fall within the true spirit and scope of the invention.

What is claimed is:

1. A surgical method, comprising:
    advancing an elongate surgical apparatus per-orally into the stomach of a patient;
    insufflating the stomach of the patient;
    deploying at least two tissue anchors connected by suture from the surgical apparatus, with the tissue anchors expanding from a delivery configuration when in the surgical apparatus to an expanded configuration when deployed from the surgical apparatus;
    placing the expanded tissue anchors into a region of gastric tissue in the patient's stomach;
    cutting an opening in the region of gastric tissue adjacent to the tissue anchors, after placing the expanded tissue anchors;
    moving a surgical tool through the opening in the region of gastric tissue with the surgical tool acting on tissue outside of the stomach;
    withdrawing the surgical tool back through the opening; and
    partially or fully closing the opening by pulling on the expanded tissue anchors.

2. The method of claim 1 further comprising cutting the opening between at least two of the expanded tissue anchors.

3. The method of claim 1 further comprising inflating a balloon at the opening.

4. The method of claim 1 further comprising determining a central location between the expanded tissue anchors, and cutting the opening at the central location.

5. The method of claim 1 further comprising drawing the at least two expanded tissue anchors towards each other by pulling on the suture, to at least partially close off the opening.

6. The method of claim 1 further comprising placing first and second pairs of expanded tissue anchors, and then cutting the opening in between the first and second pairs of expanded tissue anchors.

7. The method of claim 1 with at least one of the first and second tissue anchors comprising a plurality of reconfigurable struts extending between a distal collar and a proximal collar.

8. The method of claim 7 with the suture extending through the proximal collar of the first tissue anchor and through the distal and proximal collars of the second tissue anchor, further comprising partially or fully closing the opening by pulling on the suture.

9. A surgical method, comprising:
    advancing an elongate surgical apparatus per-orally into the stomach of a patient;
    insufflating the stomach of the patient;
    piercing a region of gastric tissue with a hollow needle extending out from the surgical apparatus;
    deploying at least two tissue anchors by pushing them out of the hollow needle, with the tissue anchors expanding from a delivery configuration when in the hollow needle to an expanded configuration when deployed from the hollow needle;
    placing the expanded tissue anchors into a region of gastric tissue in the patient's stomach;
    cutting an opening in the region of gastric tissue adjacent to the tissue anchors, after placing the tissue anchors;
    moving a surgical instrument through the opening in the region of gastric tissue with the surgical instrument acting on tissue outside of the stomach;
    withdrawing the surgical instrument back through the opening; and
    partially or fully closing the opening by moving the expanded tissue anchors towards each other.

10. The method of claim 9 with at least two of the expanded tissue anchors connected to each other by suture, and further comprising drawing the at least two expanded tissue anchors towards each other by pulling on the suture.

11. The method of claim 10 with at least one of the first and second tissue anchors comprising arm members connecting a first collar and a second collar.

12. The method of claim 11 with the suture extending through the second collar of the first tissue anchor and through the first and second collars of the second tissue anchor.

* * * * *